(12) United States Patent
Chang et al.

(10) Patent No.: US 8,871,976 B2
(45) Date of Patent: Oct. 28, 2014

(54) CHALCONE STRUCTURE FLUORESCENCE DYE FOR EMBRYONIC STEM CELL PROBE

(75) Inventors: Young-Tae Chang, Singapore (SG); Sung Chan Lee, Singapore (SG); Nam Young Kang, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 57 days.

(21) Appl. No.: 13/817,898

(22) PCT Filed: Aug. 26, 2011

(86) PCT No.: PCT/SG2011/000294
§ 371 (c)(1),
(2), (4) Date: May 6, 2013

(87) PCT Pub. No.: WO2012/026886
PCT Pub. Date: Mar. 1, 2012

(65) Prior Publication Data
US 2013/0224790 A1    Aug. 29, 2013

Related U.S. Application Data

(60) Provisional application No. 61/377,570, filed on Aug. 27, 2010.

(51) Int. Cl.

| | |
|---|---|
| *C07C 233/05* | (2006.01) |
| *C07C 233/65* | (2006.01) |
| *C07D 207/34* | (2006.01) |
| *G01N 33/58* | (2006.01) |
| *C09B 23/14* | (2006.01) |
| *C07C 235/56* | (2006.01) |
| *C07C 233/62* | (2006.01) |
| *C09K 11/06* | (2006.01) |
| *C07C 235/64* | (2006.01) |
| *C07D 213/81* | (2006.01) |
| *C07D 261/18* | (2006.01) |
| *C07C 235/16* | (2006.01) |
| *C07C 233/44* | (2006.01) |
| *C07D 213/82* | (2006.01) |
| *C07C 233/80* | (2006.01) |
| *C07D 307/68* | (2006.01) |
| *C07D 333/38* | (2006.01) |
| *C07D 333/68* | (2006.01) |
| *C07C 233/54* | (2006.01) |
| *C07D 241/24* | (2006.01) |

(52) U.S. Cl.
CPC .......... *C09B 23/143* (2013.01); *C07D 207/34* (2013.01); *G01N 33/582* (2013.01); *C09B 23/145* (2013.01); *C07C 235/56* (2013.01); *C07C 233/62* (2013.01); *C09K 11/06* (2013.01); *C07K 233/43* (2013.01); *C07C 235/64* (2013.01); *C07D 213/81* (2013.01); *C07D 261/18* (2013.01); *C07C 235/16* (2013.01); *C09K 2211/1014* (2013.01); *C07C 233/44* (2013.01); *C07D 213/82* (2013.01); *C07C 233/80* (2013.01); *C07D 307/68* (2013.01); *C07D 333/38* (2013.01); *C07D 333/68* (2013.01); *C07C 233/54* (2013.01); *C07D 241/24* (2013.01)
USPC ........... 564/221; 564/166; 564/184; 564/202; 564/207; 544/165; 544/406; 546/291; 549/489; 560/43; 435/34

(58) Field of Classification Search
USPC .......... 564/166, 184, 202, 207, 221; 544/165, 544/406; 546/291; 549/487; 560/43; 435/34
See application file for complete search history.

(56) References Cited

U.S. PATENT DOCUMENTS 2,538,009 A    1/1951    Keyes et al.

OTHER PUBLICATIONS

Mokle, S.S., et al., "Studies on Synthesis and Antimicrobial Activity of Some New Iodochalcones, Flavones and Flavonols", Int. J. Chem. Sci., 2(1), 96-100, 2004.
Im, Chang-Nim, et al., "A Fluorescent Rosamine Compound Selectively Stains Pluripotent Stem Cells", Angew Chem. Int. Ed.. 49, 7497-7500, 2010.
Ghosh, Krishna Kanta, et al., "Solid phase combinatorial synthesis of a xanthone library using click chemistry and its application to an embryonic stem cell probe", Chem. Commun., 47, 7488-7490, 2011.
Lee, Jun-Seok, et al., Accelerating fluorescent sensor discovery: unbiased screen of a diversity-oriented BODIPY library, Chem. Commun., 47, 2339-2341, 2011.
Niu, C. et al., "Fluorescence water sensor based on covalent immobilization of chalcone derivative", Analytica Chimica Acta, 577:264-270, 2006.
Kudryavtsev, V. V. et al., "Phototransformations of Substituted Chalcones under Conditions of Direct and Sensitized Photolysis", Russian Journal of General Chemistry, 70(8):1272-1280, 2000.

(Continued)

*Primary Examiner* — Shailendra Kumar
(74) *Attorney, Agent, or Firm* — Hamilton, Brook, Smith & Reynolds, P.C.

(57) ABSTRACT

The invention includes a compound represented by the following structural formula: wherein is described herein. The compounds of the invention are useful in staining embryonic stem cells.

31 Claims, 19 Drawing Sheets

(56) References Cited

OTHER PUBLICATIONS

Wang, P. and Wu, S., "Spectroscopy and photophysics of bridged enone derivatives: effect of melecular structure and solvent", Journal of Photochemistry and Photobiology, 86:109-113, 1995.
International Search Report and Written Opinion of the International Searching Authority, International Application No. PCT/SG2011/000294, International Filing Date: Aug. 26, 2011, "Chalcone Structure Fluorescence Dye for Embryonic Stem Cell Probe", Date of Communication: Oct. 21, 2011.
Lee, Sun-Chan et al., "Development of a fluorescent chalcone library and its application in the discovery of a mouse embryonic stem probe," Chem. Commun., 48:6681-6683, 2012.
Sivakumar, P. M., et al., "QSAR Studies on Chalcones and Flavonoids as Anti-tuberculosis Agents Using Genetic Function Approximation (GFA) Method", Chem. Pharm. Bull. 55(1):44-49, 2007.
Thomson, J. A. et al., "Embryonic Stem Cell Lines Derived from Human Blastocysts", www.sciencemag.org, Science, 282(6);1145-1147, Nov. 6, 1998.
Rosner, M. H., "A POU-domain transcription factor in early stem cell and germ cells of the mamalian embryo", Nature, 345: 686-692, Jun. 21, 1990.
Pesce, M. and Schöler, H. R., "Oct-4: Gatekeeper in the Beginnings of Mammalian Development", www.StemCells.com, Stem Cells 19:271-278, 2001.
Chambers, I. et al., "Functional Expression Cloning of Nanog, a Pluripotency Sustaining Factor in Embryonic Stem Cells", Cell, 113:643-655, May 30, 2003.
Mitsui, K. et al., "The Homeoprotein Nanog Is Required for Maintenance of Pluripotency in Mouse Epiblast and ES Cells", Cell, 113:631-642, May 30, 2003.
Cavaleri, F. and Schöler, H.R., "Nanog: A New Recruit to the Embryonic Stem Cell Orchestra", Cell, 113:551-557, May 30, 2003.
Solter, D. and Knowles, B. B., "Monoclonal antibody defining a stage-specific mouse embryonic antigen (SSEA-1)", Proc. Natl. Acad. Sci. USA, 75(11):5565-5569, Nov. 1978.
Kannagi, R. et al., "Stage-specific embryonic antigens (SSEA-3 and -4) are epitopes of a unique globo-series ganglioside isolated from human teratocarcinoma cells", The EMBO Journal, 2(12):2355-2361, 1983.
Thomson, J. A. et al., "Isolation of a primate embryonic stem cell line", Proc. Natl. Acad. Sci. USA 92:7844-7848, Aug. 1995.
Shamblott, M. J. et al., "Derivation of pluripotent stem cells from cultured human primordial germ cells", Proc. Natl. Acad. Sci. USA, 95:13726-13731, Nov. 1998.
Miranda C L, et al., "Antioxcidan and Prooxidant Actions of Prenylated and Nonprenylated Chalcones and Flavanones in Vitro", J. Agric. Food Chem, 48:3876-3884, 2000.
Satyanarayana M, et al., "Synthesis and antihyperglycemic Activity of chalcone based aryloxypropanolamines", Bioorg. Med. Chem., 12:883-889, 2004.
Barford L, et al., "Chalcones from Chinese liquorice inhibit proliferation of T cells and production of cytokines", Int. Immunopharmacol, 2:545-555, 2002.
Wang, P.F., Spectroscopy and photophysics of bridged enone derivatives: effect of melecular structure and solvent:, S.K. Wu, J. Photochem. Photobiol. A Chemistry 86:109-113, 1995.
C-G Niu, et al., "Fluorescene water sensor based on covalent immobilization of chalcone derivative", Analytica Chimica Acta 577:264-270, 2006.
Niwa, H. et al., "Quantitative expression of Oct-3/4 defines differentiation, dedifferentiation or self-renewal of ES cells", Nat. Genet. 24:372, 2000.
Knowles, B. B. et al., "Expression of H-2 laminin and SV40 T and TASA on differentiation of transformed murine teratocarcinoma cells", Nature 288:615, Dec. 1980.
Shevinsky, L.H. et al., "Monoclonal Antibody to Murine Embryos Defines a Stage-Specific Embryonic Antigen Expressed on Mouse Embroyos and Human Teratocarcinoma Cells", Cell 30:697-705, 1982.
Federson, B. A. et al., "Glycoconjugate Expression during Embryogenesis and its Biological Significance", BioEssays 12(4):173, Apr. 1990.
Thomson, J.A. et al., "Primate Embryonic Stem Cells", Curr. Top. Dev. Biol., 38:133, 1998.
Hsieh H K, et al., "Synthesis and Anti-inflammatory Effect of Chalcones", J. Pharm. Pharmacol., 52:163-171, 2000.
Millan, J.L. and W.H. Fishman, "Biology of Human Alkaline Phosphatases with Special Reference to Cancer", Crit Rev Clin Lab Sci. 32(1):1-39, 1995.
Viana G S, et al., "Analgesic and antiinflammatory effectes of chalcones isolated from *Myracrodruon urundeuva* Allemao", J. Phytomedicine, 10:189-195, 2003.
Zhao L M, et al., "Synethesis and evaluation of antiplatelet activity of trihydroxychalcone derivatives", Bioorg. Med. Chem. Lett, 15:5027-5029, 2005.
Mukarami S, et al., "Inhibition of Gastric H+, K+-ATPase by the Anti-Ulcer Agent, Sofalcone", Biochem. Pharmacol, 42(7):1447-1451, 1991.
Liu M, et al., "Antimalarial Alkoxylated and Hydroxylated Chalones: Structure-Activity Relationship Analysis", J. Med. Chem, 44:4443-4452, 2001.
Epifano, F. et al., "Chemistry and pharmacology of oxyprenylated secondary plant metabolites", Phytochem, 68: 939-953, 2007.
Onyilagna J C, et al., "Comparative studies of inhibitory activites of chalcones on tomato ringspot virus (ToRSV)" Can. J. Plant Pathol, 1997,19(2):133-137.
Nielsen S F, et al., "Synthesis of Antiparasitic Licorice Chalcones", Bioorg. Med. Chem. Lett, 5(5):449-452, 1995.

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-1 | 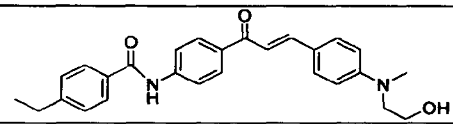 | 429.2 | 429.0 | 431 | 560 | 126061 | 0.190 |
| CLA-2 | 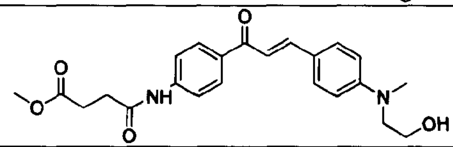 | 411.2 | 411.0 | 428 | 555 | 25115 | 0.171 |
| CLA-4 | 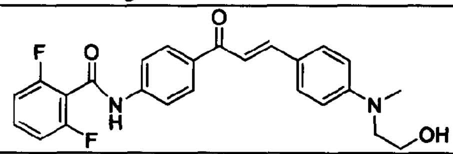 | 437.2 | 437.0 | 431 | 565 | 96339 | 0.146 |
| CLA-5 | 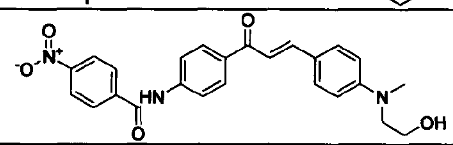 | 446.2 | 446.0 | 433 | 551 | 75879 | 0.003 |
| CLA-6 | 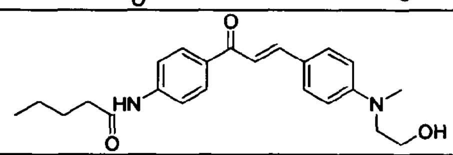 | 381.2 | 381.0 | 427 | 557 | 37091 | 0.200 |
| CLA-7 | 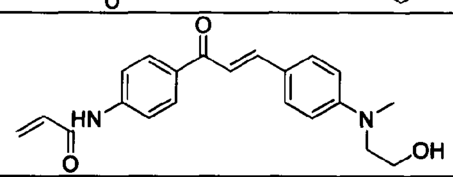 | 351.2 | 351.0 | 429 | 563 | 23564 | 0.202 |
| CLA-8 | 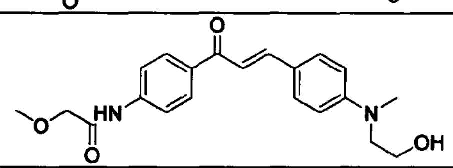 | 369.2 | 369.0 | 429 | 556 | 27442 | 0.164 |
| CLA-10 | 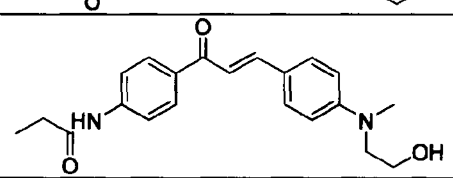 | 353.2 | 353.0 | 427 | 554 | 28994 | 0.181 |
| CLA-12 | 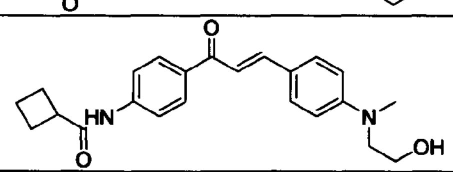 | 379.2 | 379.0 | 428 | 556 | 34036 | 0.208 |
| CLA-14 | 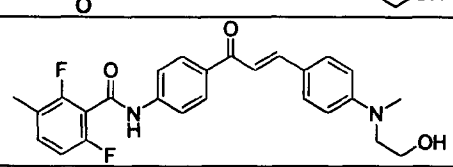 | 451.2 | 450.9 | 431 | 565 | 37479 | 0.150 |

FIG. 1

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-15 | 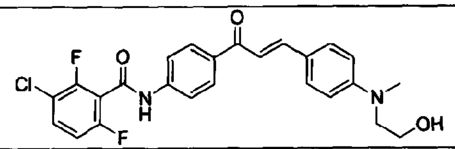 | 471.1 | 470.9 | 433 | 568 | 49115 | 0.130 |
| CLA-16 | 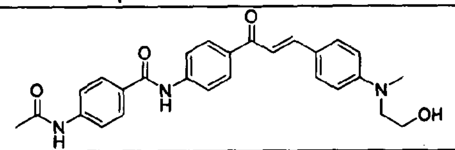 | 458.2 | 458.0 | 431 | 593 | 127564 | 0.182 |
| CLA-17 | 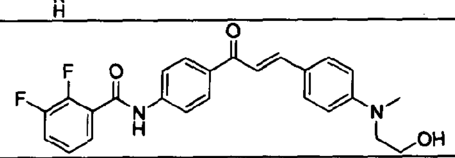 | 437.2 | 437.0 | 432 | 564 | 46545 | 0.147 |
| CLA-18 | 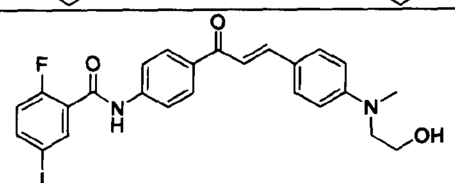 | 545.1 | 544.8 | 431 | 567 | 56533 | 0.149 |
| CLA-20 | 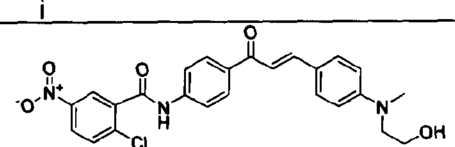 | 480.1 | 479.9 | 432 | 544 | 67152 | 0.010 |
| CLA-22 | 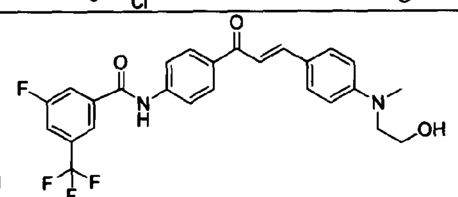 | 487.2 | 486.9 | 432 | 563 | 40970 | 0.048 |
| CLA-23 | 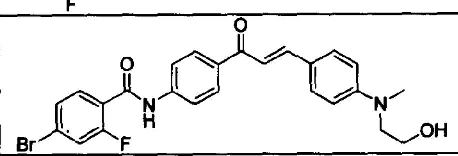 | 497.1 | 498.8 | 433 | 561 | 26376 | 0.117 |
| CLA-24 | 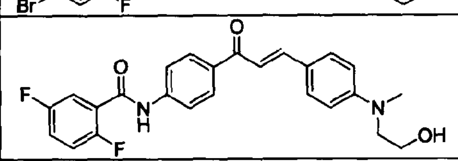 | 437.2 | 436.9 | 432 | 564 | 40970 | 0.131 |
| CLA-25 | 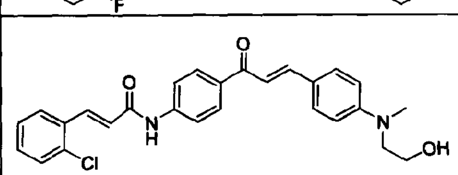 | 461.2 | 460.9 | 430 | 551 | 12412 | 0.016 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-26 | 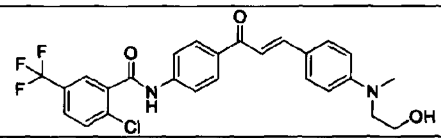 | 503.1 | 504.1 | 431 | 564 | 50715 | 0.129 |
| CLA-27 | 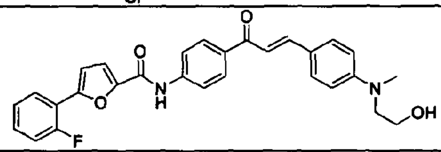 | 485.2 | 485.0 | 431 | 567 | 61430 | 0.133 |
| CLA-28 | 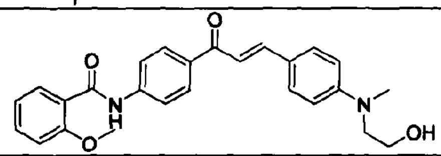 | 431.2 | 431.0 | 430 | 561 | 54642 | 0.154 |
| CLA-29 | 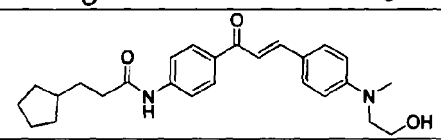 | 421.2 | 421.1 | 428 | 557 | 46303 | 0.163 |
| CLA-31 | 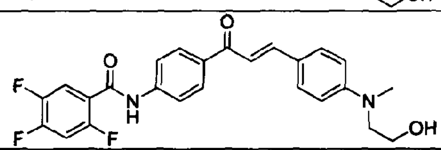 | 455.2 | 454.9 | 431 | 562 | 32388 | 0.118 |
| CLA-32 | 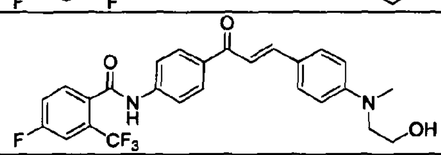 | 487.2 | 486.9 | 431 | 560 | 56970 | 0.146 |
| CLA-33 | 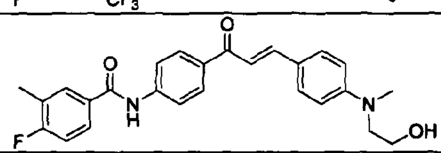 | 433.2 | 433.0 | 430 | 563 | 53236 | 0.148 |
| CLA-35 | 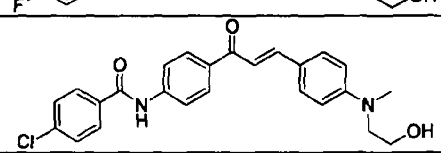 | 435.1 | 434.9 | 431 | 562 | 48485 | 0.154 |
| CLA-36 | 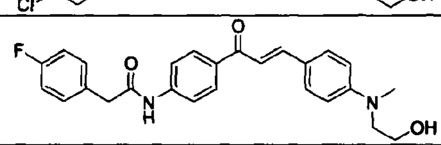 | 433.2 | 433.0 | 429 | 557 | 39952 | 0.161 |
| CLA-37 | 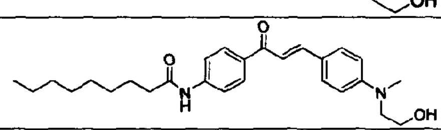 | 437.3 | 437.1 | 427 | 554 | 17648 | 0.148 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-38 | (structure) | 431.2 | 431.0 | 431 | 562 | 52461 | 0.150 |
| CLA-41 | (structure) | 467.1 | 466.9 | 431 | 563 | 56533 | 0.131 |
| CLA-42 | (structure) | 415.2 | 415.0 | 430 | 562 | 59103 | 0.140 |
| CLA-44 | (structure) | 423.3 | 423.1 | 428 | 556 | 45382 | 0.139 |
| CLA-45 | (structure) | 466.1 | 465.9 | 432 | 550 | 58861 | 0.018 |
| CLA-46 | (structure) | 480.1 | 479.9 | 431 | 561 | 56824 | 0.039 |
| CLA-47 | (structure) | 491.1 | 490.9 | 431 | 555 | 27200 | 0.027 |
| CLA-49 | (structure) | 392.2 | 392.0 | 433 | 569 | 47806 | 0.054 |
| CLA-50 | (structure) | 521.1 | 520.9 | 431 | 563 | 50279 | 0.118 |
| CLA-51 | (structure) | 453.1 | 452.9 | 431 | 563 | 16970 | 0.111 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-52 | 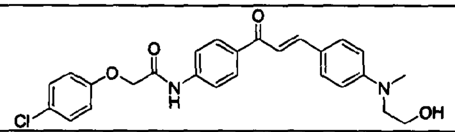 | 465.2 | 464.9 | 430 | 562 | 59830 | 0.132 |
| CLA-53 | 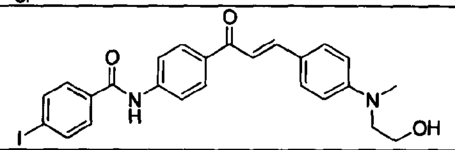 | 527.1 | 526.8 | 431 | 564 | 71176 | 0.159 |
| CLA-54 | 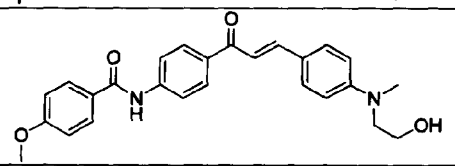 | 431.2 | 431.0 | 430 | 559 | 74036 | 0.146 |
| CLA-55 | 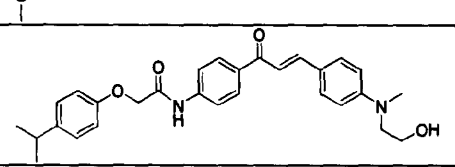 | 473.2 | 473.0 | 430 | 561 | 73212 | 0.130 |
| CLA-57 | 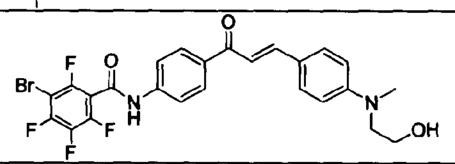 | 551.1 | 550.7 | 432 | 568 | 78885 | 0.091 |
| CLA-58 | 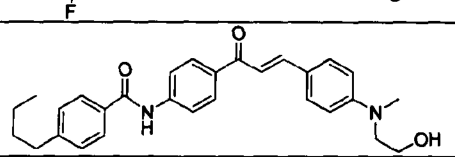 | 457.2 | 457.0 | 429 | 561 | 51103 | 0.141 |
| CLA-59 | 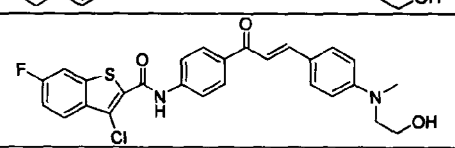 | 509.1 | 508.9 | 430 | 539 | 42133 | 0.054 |
| CLA-61 | 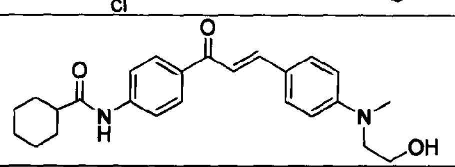 | 407.2 | 407.0 | 429 | 553 | 57697 | 0.174 |
| CLA-62 | 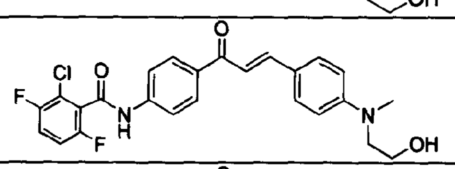 | 471.1 | 470.9 | 432 | 564 | 62061 | 0.127 |
| CLA-64 | 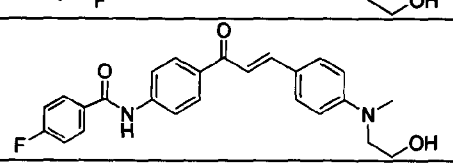 | 419.2 | 418.9 | 430 | 565 | 21091 | 0.166 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-65 | 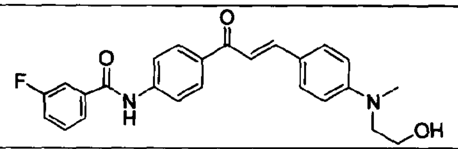 | 419.2 | 419.0 | 431 | 565 | 60655 | 0.136 |
| CLA-66 | 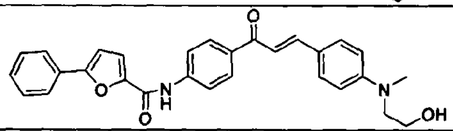 | 467.2 | 466.9 | 431 | 567 | 67006 | 0.138 |
| CLA-68 | 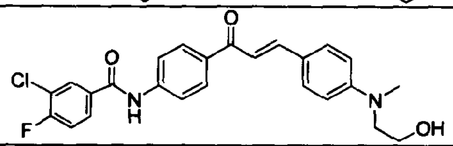 | 453.1 | 452.9 | 431 | 566 | 69721 | 0.128 |
| CLA-69 | 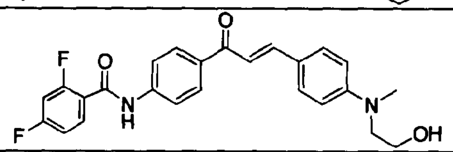 | 437.2 | 436.9 | 431 | 564 | 49455 | 0.129 |
| CLA-70 | 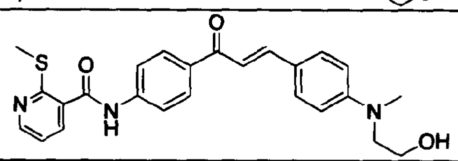 | 448.2 | 447.9 | 431 | 565 | 62061 | 0.133 |
| CLA-71 | 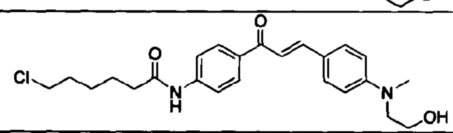 | 429.2 | 429.0 | 429 | 557 | 51248 | 0.135 |
| CLA-72 | 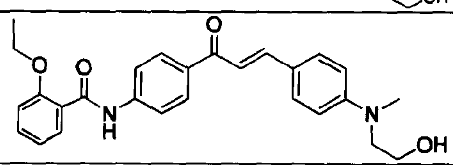 | 445.2 | 445.0 | 429 | 561 | 61673 | 0.142 |
| CLA-73 | 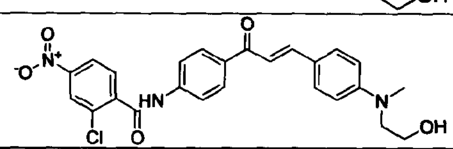 | 480.1 | 479.8 | 432 | 540 | 67830 | 0.008 |
| CLA-74 | 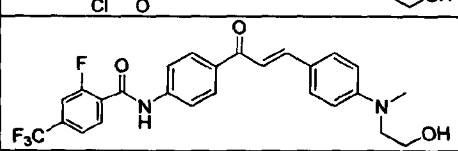 | 487.2 | 486.9 | 431 | 560 | 57261 | 0.050 |
| CLA-75 | 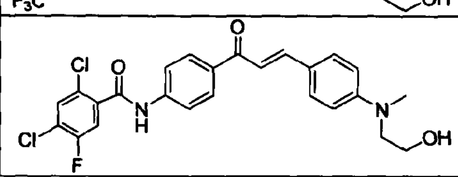 | 487.1 | 486.8 | 431 | 564 | 26521 | 0.119 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-76 | 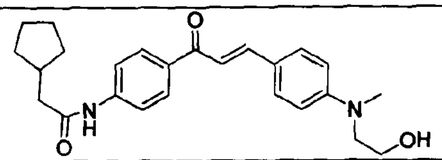 | 407.2 | 407.0 | 429 | 556 | 55127 | 0.159 |
| CLA-77 | 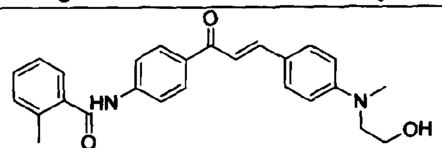 | 415.2 | 415.0 | 430 | 562 | 87273 | 0.136 |
| CLA-78 | 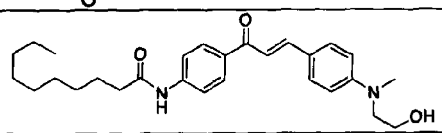 | 451.3 | 451.0 | 427 | 555 | 61770 | 0.127 |
| CLA-79 | 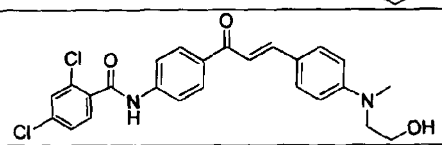 | 469.1 | 468.9 | 431 | 564 | 88097 | 0.117 |
| CLA-80 | 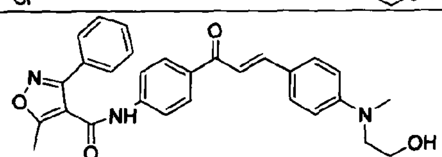 | 482.2 | 482.0 | 431 | 561 | 84024 | 0.120 |
| CLA-81 | 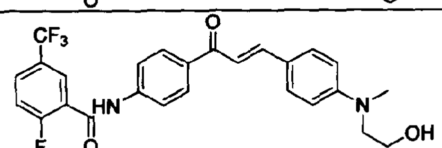 | 487.2 | 486.9 | 431 | 563 | 85915 | 0.078 |
| CLA-82 | 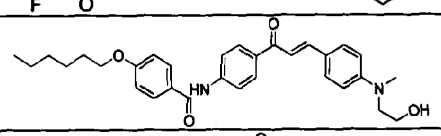 | 501.3 | 501.0 | 429 | 561 | 89503 | 0.155 |
| CLA-83 | 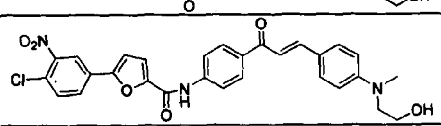 | 546.1 | 545.8 | 430 | 545 | 82667 | 0.020 |
| CLA-84 | 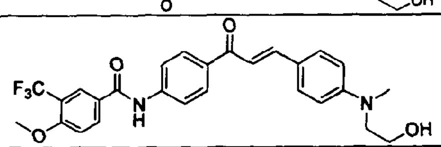 | 499.2 | 498.9 | 431 | 563 | 88291 | 0.138 |
| CLA-85 | 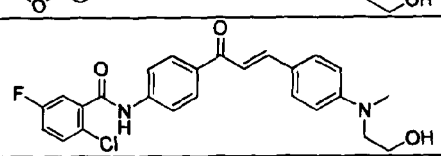 | 453.1 | 452.9 | 429 | 565 | 16000 | 0.137 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-86 | 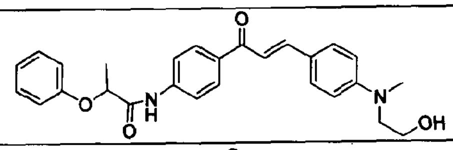 | 445.2 | 445.0 | 430 | 562 | 66861 | 0.125 |
| CLA-87 | 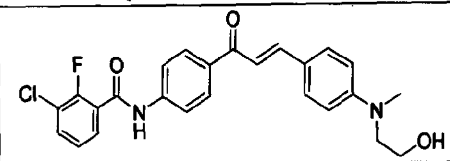 | 453.1 | 452.9 | 432 | 566 | 87418 | 0.107 |
| CLA-88 | 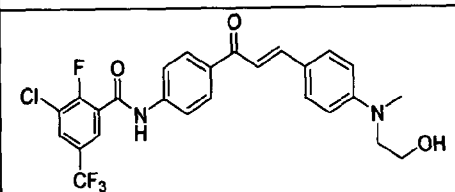 | 521.1 | 520.8 | 433 | 563 | 92170 | 0.043 |
| CLA-90 | 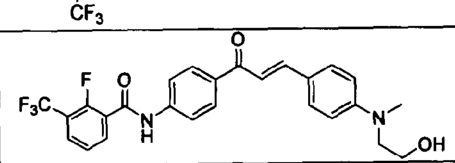 | 487.2 | 486.9 | 432 | 565 | 95952 | 0.102 |
| CLA-91 | 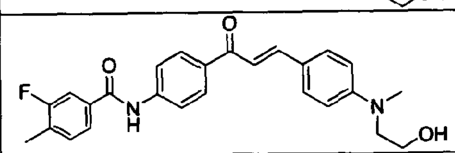 | 433.2 | 433.0 | 432 | 566 | 92170 | 0.116 |
| CLA-92 | 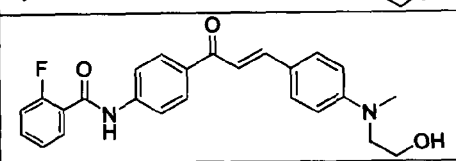 | 419.2 | 418.9 | 431 | 564 | 117285 | 0.121 |
| CLA-94 | 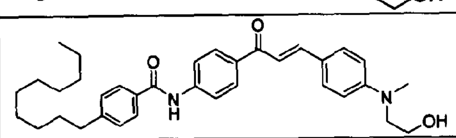 | 541.3 | 541.2 | 429 | 563 | 56145 | 0.134 |
| CLA-95 | 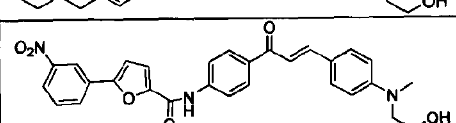 | 512.2 | 511.9 | 432 | 549 | 160242 | 0.016 |
| CLA-96 | 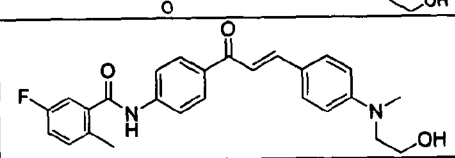 | 433.2 | 433.0 | 431 | 562 | 119127 | 0.135 |
| CLA-97 | 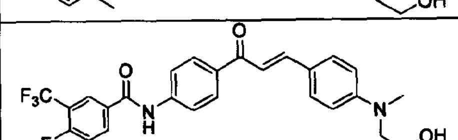 | 487.2 | 486.9 | 432 | 565 | 56679 | 0.126 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-98 | 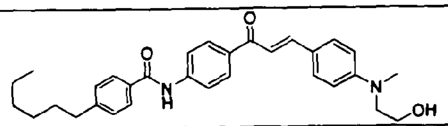 | 485.3 | 485.0 | 428 | 562 | 115345 | 0.120 |
| CLA-99 | 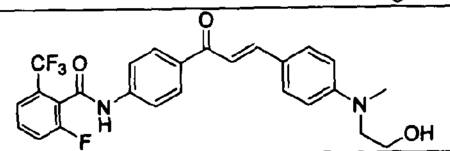 | 487.2 | 486.9 | 431 | 565 | 81067 | 0.107 |
| CLA-100 | 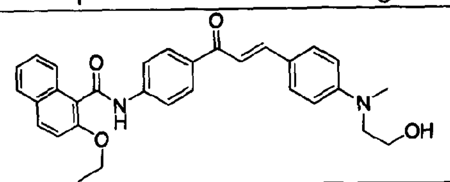 | 495.2 | 495.0 | 430 | 563 | 83879 | 0.148 |
| CLA-102 | 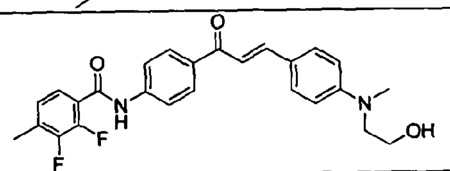 | 451.2 | 451.0 | 431 | 564 | 78255 | 0.135 |
| CLA-103 | 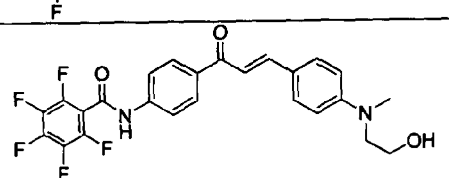 | 491.1 | 490.9 | 432 | 570 | 38642 | 0.110 |
| CLA-104 | 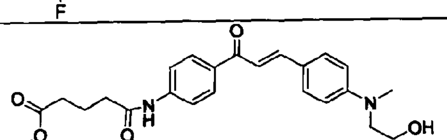 | 425.2 | 425.0 | 429 | 559 | 36945 | 0.179 |
| CLA-105 | 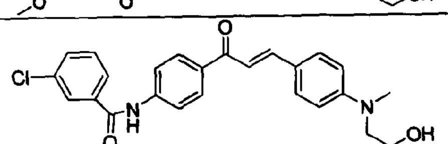 | 435.1 | 434.9 | 431 | 565 | 52800 | 0.163 |
| CLA-106 | 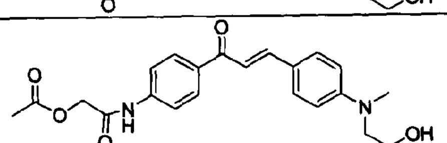 | 397.2 | 397.0 | 427 | 558 | 17115 | 0.193 |
| CLA-107 | 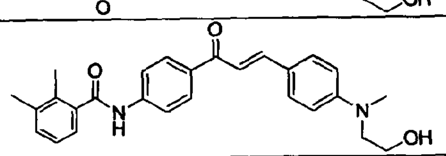 | 429.2 | 429.0 | 429 | 562 | 55661 | 0.183 |
| CLA-108 | 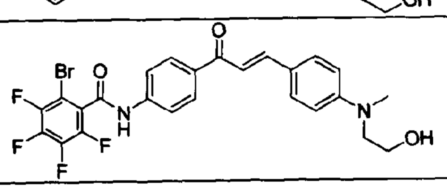 | 551.1 | 550.8 | 432 | 568 | 45042 | 0.125 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-109 | 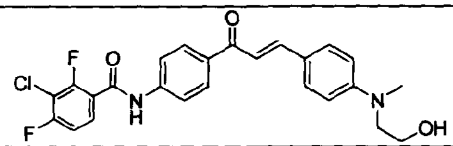 | 471.1 | 470.9 | 432 | 568 | 49697 | 0.117 |
| CLA-110 | 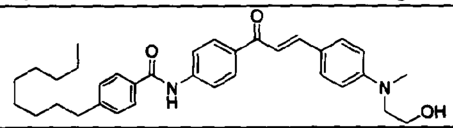 | 527.3 | 527.0 | 428 | 560 | 40679 | 0.129 |
| CLA-111 | 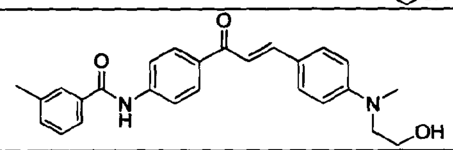 | 415.2 | 415.0 | 430 | 561 | 53867 | 0.167 |
| CLA-112 | 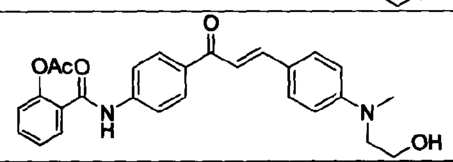 | 459.2 | 458.9 | 430 | 563 | 54594 | 0.161 |
| CLA-114 | 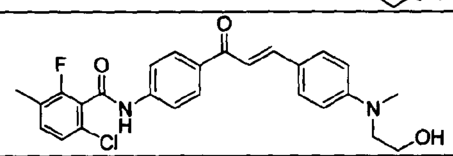 | 467.1 | 466.9 | 431 | 563 | 54691 | 0.155 |
| CLA-115 | 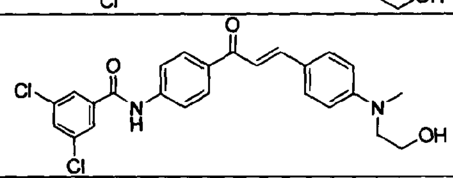 | 469.1 | 468.9 | 431 | 563 | 55758 | 0.076 |
| CLA-116 | 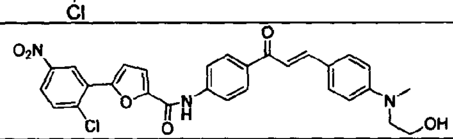 | 546.1 | 545.9 | 432 | 544 | 139588 | 0.006 |
| CLA-117 | 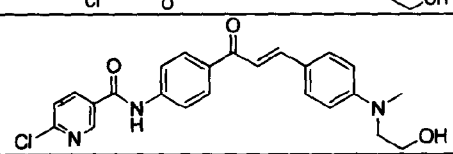 | 436.1 | 435.9 | 431 | 565 | 45091 | 0.132 |
| CLA-119 | 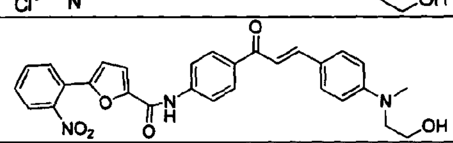 | 512.2 | 511.9 | 431 | 547 | 60994 | 0.015 |
| CLA-120 | 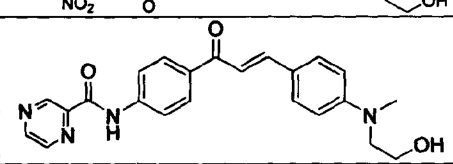 | 403.2 | 402.9 | 431 | 542 | 35782 | 0.026 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-121 | 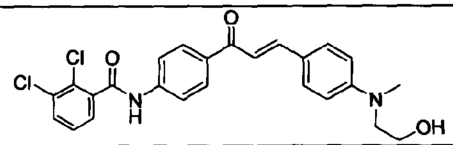 | 469.1 | 468.9 | 431 | 565 | 62061 | 0.129 |
| CLA-122 | 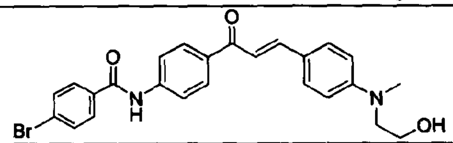 | 479.1 | 478.9 | 431 | 564 | 59782 | 0.127 |
| CLA-123 | 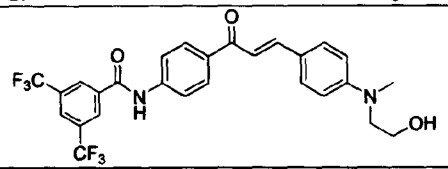 | 537.2 | 536.9 | 432 | 559 | 59539 | 0.023 |
| CLA-124 | 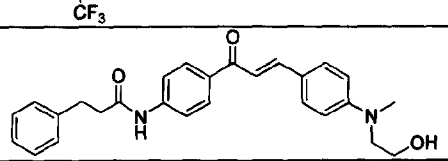 | 429.2 | 429.0 | 428 | 556 | 55564 | 0.163 |
| CLA-127 | 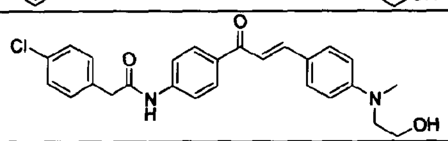 | 449.2 | 448.9 | 428 | 557 | 33503 | 0.168 |
| CLA-128 | 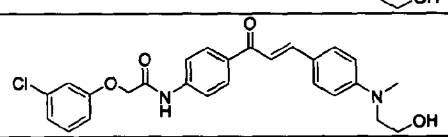 | 465.2 | 464.9 | 430 | 559 | 64048 | 0.153 |
| CLA-129 | 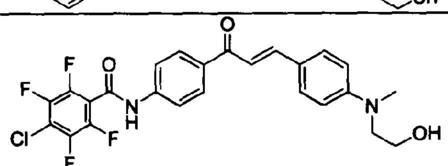 | 507.1 | 506.8 | 432 | 564 | 34085 | 0.052 |
| CLA-130 | 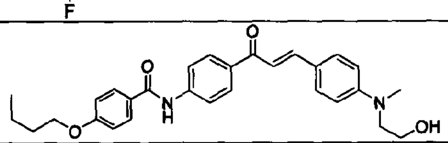 | 473.2 | 473.0 | 429 | 560 | 55321 | 0.201 |
| CLA-131 | 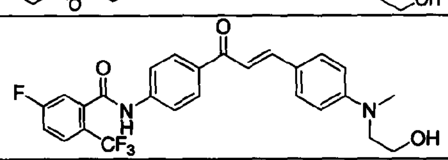 | 487.2 | 486.9 | 431 | 563 | 51539 | 0.153 |
| CLA-132 | 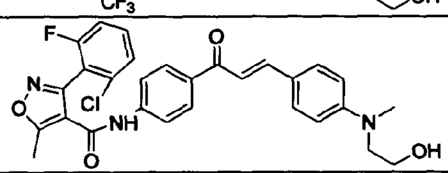 | 534.2 | 534.0 | 427 | 553 | 49309 | 0.150 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-134 | 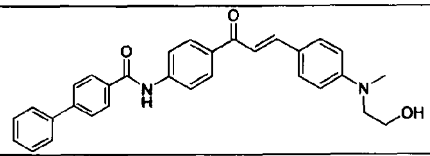 | 477.2 | 477.0 | 439 | 582 | 129891 | 0.159 |
| CLA-136 | 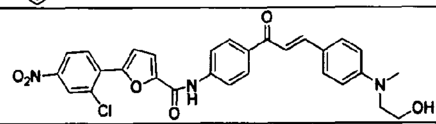 | 546.1 | 545.8 | 429 | 543 | 29139 | 0.029 |
| CLA-137 | 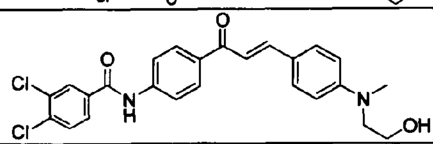 | 469.1 | 469.0 | 425 | 563 | 18764 | 0.119 |
| CLA-138 | 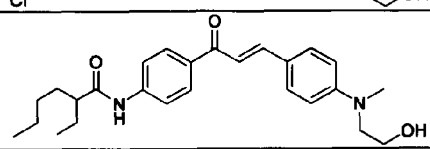 | 423.3 | 423.0 | 428 | 552 | 43539 | 0.203 |
| CLA-140 | 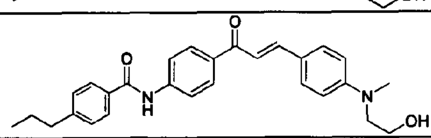 | 443.2 | 443.0 | 428 | 560 | 41406 | 0.202 |
| CLA-142 | 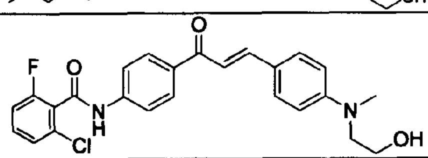 | 453.1 | 452.9 | 431 | 563 | 57164 | 0.165 |
| CLA-143 | 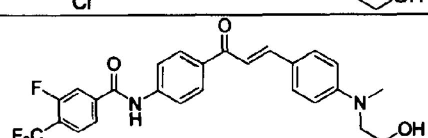 | 487.2 | 486.9 | 431 | 545 | 44315 | 0.032 |
| CLA-144 | 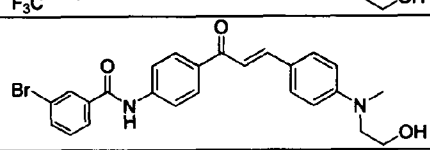 | 479.1 | 478.9 | 430 | 560 | 50473 | 0.187 |
| CLA-145 | 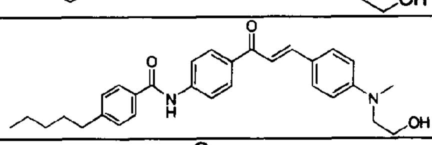 | 471.3 | 471.0 | 429 | 562 | 44606 | 0.177 |
| CLA-146 | 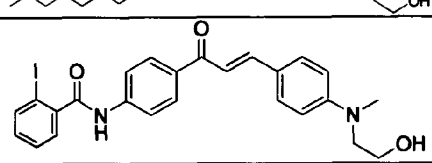 | 527.1 | 526.8 | 429 | 561 | 38158 | 0.178 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-147 | 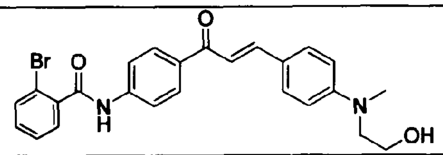 | 479.1 | 478.8 | 430 | 562 | 52945 | 0.141 |
| CLA-148 | 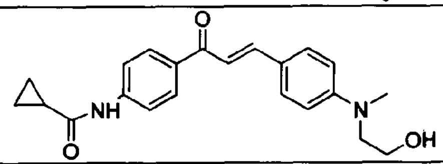 | 365.2 | 365.0 | 426 | 557 | 25309 | 0.177 |
| CLA-150 | 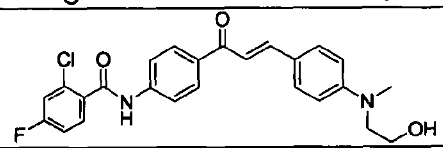 | 453.1 | 452.9 | 431 | 563 | 52315 | 0.157 |
| CLA-152 | 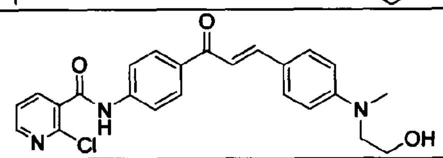 | 436.1 | 437.1 | 429 | 563 | 22109 | 0.171 |
| CLA-153 | 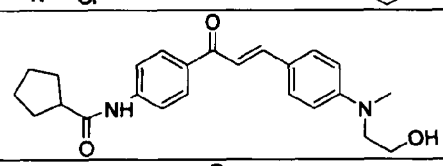 | 393.2 | 394.2 | 426 | 553 | 26230 | 0.220 |
| CLA-155 | 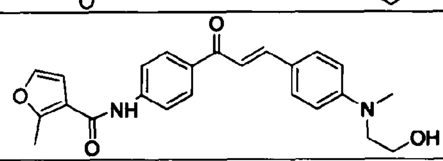 | 405.2 | 406.2 | 426 | 557 | 21333 | 0.179 |
| CLA-156 | 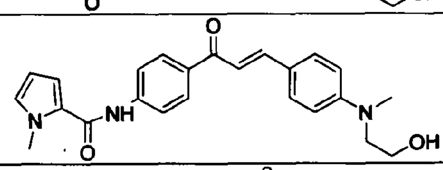 | 404.2 | 404.0 | 428 | 556 | 38691 | 0.213 |
| CLA-158 | 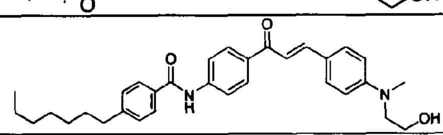 | 499.3 | 499.0 | 426 | 559 | 36461 | 0.182 |
| CLA-159 | 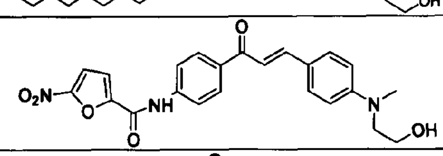 | 436.1 | 436.0 | 429 | 555 | 45091 | 0.106 |
| CLA-161 | 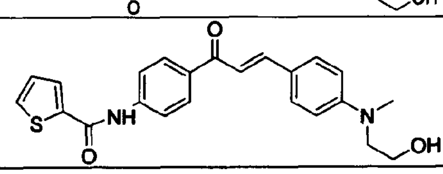 | 407.1 | 406.9 | 429 | 563 | 39321 | 0.141 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-164 | 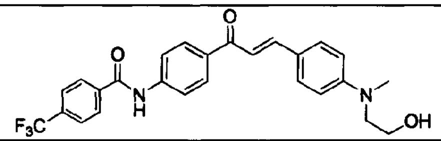 | 469.2 | 468.9 | 431 | 565 | 58909 | 0.099 |
| CLA-165 | 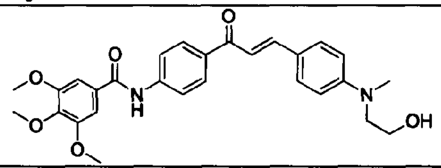 | 491.2 | 491.0 | 430 | 566 | 58327 | 0.136 |
| CLA-166 | 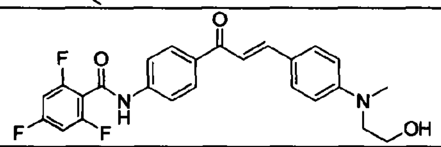 | 455.2 | 454.9 | 433 | 565 | 58036 | 0.118 |
| CLA-167 | 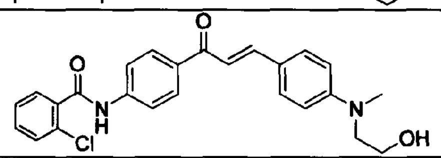 | 435.1 | 434.9 | 431 | 564 | 54933 | 0.147 |
| CLA-169 | 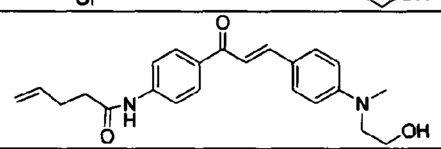 | 379.2 | 379.0 | 428 | 557 | 43345 | 0.178 |
| CLA-170 | 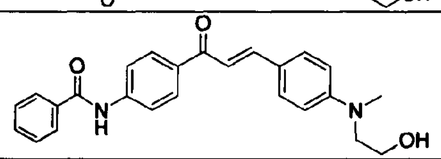 | 401.2 | 401.0 | 430 | 563 | 49261 | 0.175 |
| CLA-171 | 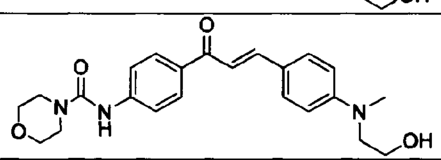 | 410.2 | 410.0 | 425 | 537 | 70158 | 0.159 |
| CLA-172 | 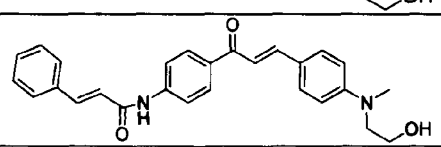 | 427.2 | 427.0 | 430 | 563 | 62448 | 0.041 |
| CLA-173 | 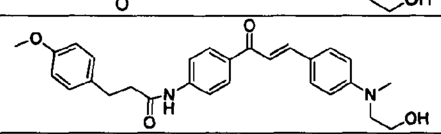 | 459.2 | 459.0 | 429 | 558 | 72339 | 0.163 |
| CLA-174 | 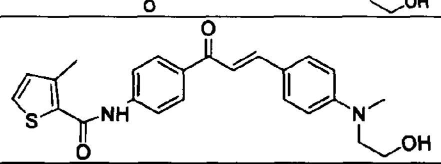 | 421.2 | 420.9 | 430 | 559 | 52121 | 0.137 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-175 | 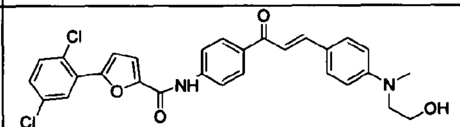 | 535.1 | 534.8 | 430 | 567 | 71612 | 0.079 |
| CLA-176 | 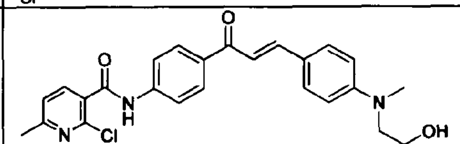 | 450.2 | 449.9 | 432 | 568 | 67539 | 0.114 |
| CLA-177 | 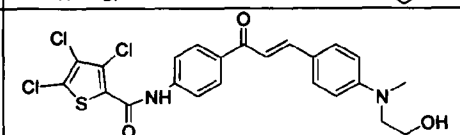 | 509.0 | 508.7 | 429 | 548 | 22497 | 0.022 |
| CLA-178 | 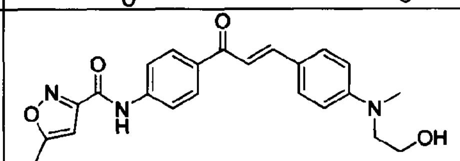 | 406.2 | 406.0 | 431 | 569 | 42764 | 0.131 |
| CLA-179 | 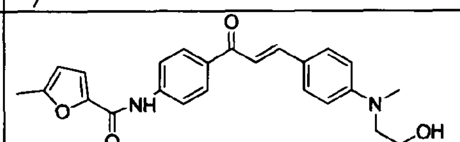 | 405.2 | 405.0 | 431 | 565 | 81600 | 0.147 |
| CLA-180 | 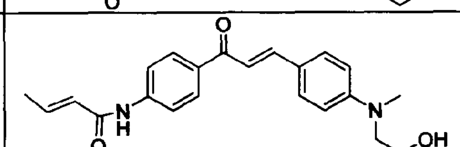 | 365.2 | 365.0 | 429 | 562 | 47127 | 0.180 |
| CLA-181 | 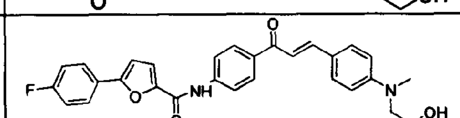 | 485.2 | 484.9 | 432 | 565 | 78788 | 0.168 |
| CLA-182 | 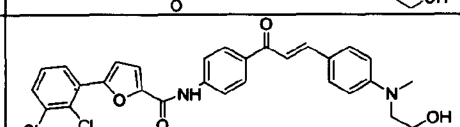 | 535.1 | 534.8 | 431 | 564 | 60364 | 0.107 |
| CLA-183 | 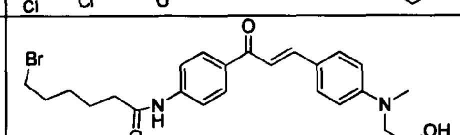 | 473.1 | 474.9 | 428 | 562 | 57552 | 0.177 |
| CLA-185 | 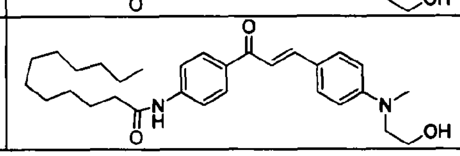 | 479.3 | 479.0 | 414 | 552 | 18327 | 0.117 |

FIG. 1 (Cont.)

Chalcone Library List

| Code | Structure | mass (calc) | mass (found) | Abs (nm) | Em (nm) | Ext Coeff | Quantum Yield (5μM) |
|---|---|---|---|---|---|---|---|
| CLA-186 | 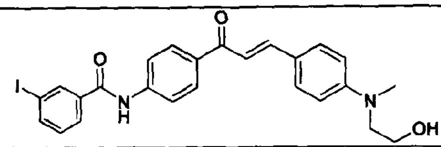 | 527.1 | 526.8 | 431 | 569 | 50861 | 0.128 |
| CLA-188 | 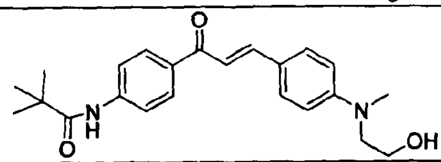 | 381.2 | 381.0 | 429 | 561 | 81988 | 0.125 |
| CLA-190 | 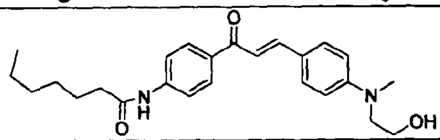 | 409.2 | 409.0 | 428 | 561 | 66909 | 0.138 |
| CLA-192 | 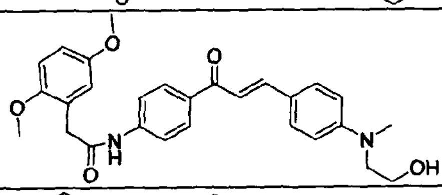 | 475.2 | 475.0 | 429 | 560 | 74036 | 0.158 |
| CLA-193 | 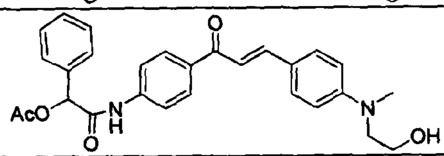 | 473.2 | 473.0 | 432 | 565 | 52121 | 0.128 |
| CLA-194 | 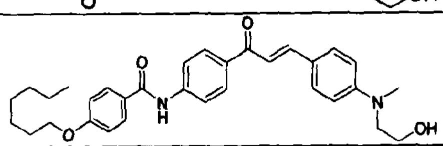 | 515.3 | 515.0 | 425 | 563 | 49358 | 0.131 |
| CLA-195 | 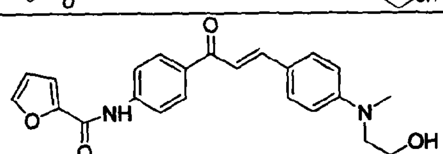 | 391.2 | 391.0 | 430 | 566 | 56921 | 0.180 |
| CLA-197 | 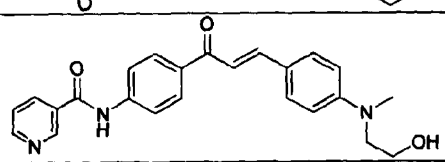 | 402.2 | 402.0 | 428 | 563 | 41600 | 0.172 |
| CLA-203 | 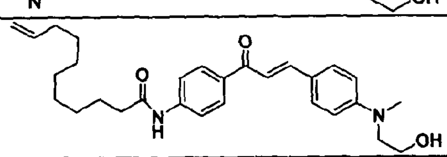 | 463.3 | 463.0 | 423 | 557 | 32048 | 0.180 |
| CLA-409 | 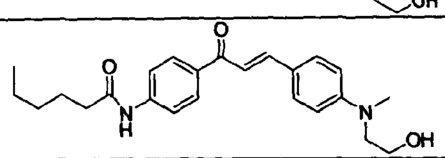 | 395.2 | 395.0 | 428 | 559 | 55467 | 0.153 |

FIG. 1 (Cont.)

Chalcone Library List

| Code | Structure | mass (calc) | mass (found) | Abs (nm) | Em (nm) | Ext Coeff | Quantum Yield (5µM) |
|---|---|---|---|---|---|---|---|
| CLA-410 | 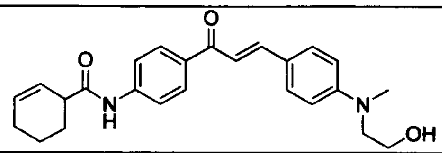 | 405.2 | 405.0 | 428 | 562 | 56533 | 0.138 |

FIG. 1 (Cont.)

CHALCONE STRUCTURE FLUORESCENCE DYE FOR EMBRYONIC STEM CELL PROBE

RELATED APPLICATION

This application is the U.S. National Stage of International Application No. PCT/SG2011/000294, filed Aug. 26, 2011, which designates the U.S., published in English, and claims the benefit of U.S. Provisional Application No. 61/377,570, filed on Aug. 27, 2010. The entire teachings of the above applications are incorporated herein by reference.

BACKGROUND OF THE INVENTION

Fluorescence detection is an indispensable technique for the analysis of a variety of biological phenomena. During the past few decades, a number of small molecule fluorescent chemosensors have been developed for use in biological analyses, which typically are elaborately designed to selectively detect a target substance or phenomenon. (See (a) Geddes, C. D.; Lakowicz, J. R., *Topics in Fluorescence Spectroscopy*, Vol. 9; Springer: New York, 2005. (b) Geddes, C. D.; Lakowicz, J. R. *Topics in Fluorescence Spectroscopy*, Vol. 10; Springer: New York, 2005, the teachings of both are incorporated herein by reference).

Embryonic stem cells (ESCs) are derived from the inner cell mass (ICM) of blastocyst-stage embryos and have the ability to self-renew indefinitely. ESCs are pluripotent because they have the capacity to give rise to differentiated progeny representative of all three embryonic germ layers, as well as the extraembryonic tissues that support development. In mammals, the property of pluripotentiality is restricted to the oocyte, the zygote, early embryonic cells, primordial germ cells, and the stem cells of tumors derived from pluripotential cells (embryonal carcinomas).

ESCs can be characterized by high level expression of Oct-3/4 (also termed Oct-3 or Oct-4), a member of the POU transcription factors, and Nanog. A critical amount of Oct-3/4 and Nanog expression is required to sustain stem-cell pluripotency. When ES cells are induced to differentiate, Oct-3/4 and Nanog are down-regulated, which has proven to be essential for a proper and divergent developmental program. Each stage of ESC differentiation can be monitored by immunocytochemistry methods. The methods for probing mouse embryonic stem cell are generally diagnosed by cell surface antibody such as Nanog, Oct4 or GFP fluorescence protein. However, these protocols are limited mainly because of late stage of stem cell differentiation and selectivity.

Therefore, there is a need for a means by which the differentiation process can be monitored, which can reduce or eliminate one or more of the above-mentioned problems.

SUMMARY OF THE INVENTION

The invention is based on the synthesis of a new fluorescence dye of chalcone structure which shows fluorescence emission sensitivity depending on the polarity and pH of the solvent. The chalcone derivatives possess a central ketone group having electron accepting properties which can make these compounds suitable for use as fluorescence emission dyes.

One embodiment of the invention is a compound represented by the following structural formula:

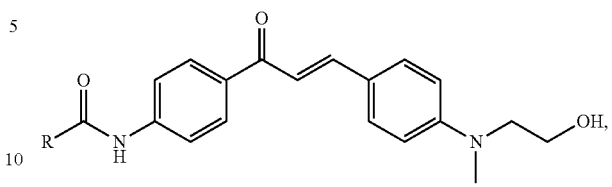

or a salt thereof, wherein:
R is $(C_1$-$C_{16})$alkyl, $(C_2$-$C_{16})$alkenyl, $(C_2$-$C_{16})$alkynyl, carbocyclyl or heterocyclyl, each of which is optionally substituted with one or more groups independently selected from the following: halo, $NO_2$, —$NHCO(C_1$-$C_6)$alkyl, —$OCO(C_1$-$C_6)$alkyl, —$COO(C_1$-$C_6)$alkyl, $(C_1$-$C_{10})$alkyl, halo$(C_1$-$C_{10})$alkyl, $(C_1$-$C_{10})$alkoxy, —$S(C_1$-$C_6)$alkyl, $(C_3$-$C_9)$cycloalkyl, aryl, and phenoxy, wherein each phenoxy or aryl are further optionally substituted with one or more groups selected from halo, $NO_2$, $(C_1$-$C_{10})$alkyl, halo$(C_1$-$C_{10})$alkyl, and $(C_1$-$C_{10})$alkoxy.

The chalcone derivatives described herein possess fluorescence emission profiles useful for staining specific embryonic stem cell. The chalcone scaffold is compatible with a range of chemical functional groups, and can be bioconjugated to proteins as well as other macromolecules of interest. As described herein, chalcone derivatives of the invention selectively stain mouse embryonic stem population and MEF feeder cells. The chalcone derivatives can be used as new probes for ES and are useful for understanding early iPS generation mechanisms. Furthermore, the chalcone derivatives may be used to elucidate new biomarkers in ESC.

CDg4 (compound identified as CLA-7 in FIG. 1) stained the early stage of embryonic stem cell differentiation, which allowed for selective sorting and isolation from mixture of Feeder cells even up to day 5. Therefore, sorting of embryonic stem cell from feeder cell after inducer treatment can be accomplished using the chalcone derivatives of the invention.

BRIEF DESCRIPTION OF THE DRAWINGS

FIG. 1 is a chart showing the chalcone compounds of the invention. The chart includes mass (calculated), mass (found), absorbtion (Abs), emission (Em), extinction coefficient (Ext Coeff) and quantum yield (5 μM) data for the compounds.

DETAILED DESCRIPTION OF THE INVENTION

Figure 2:
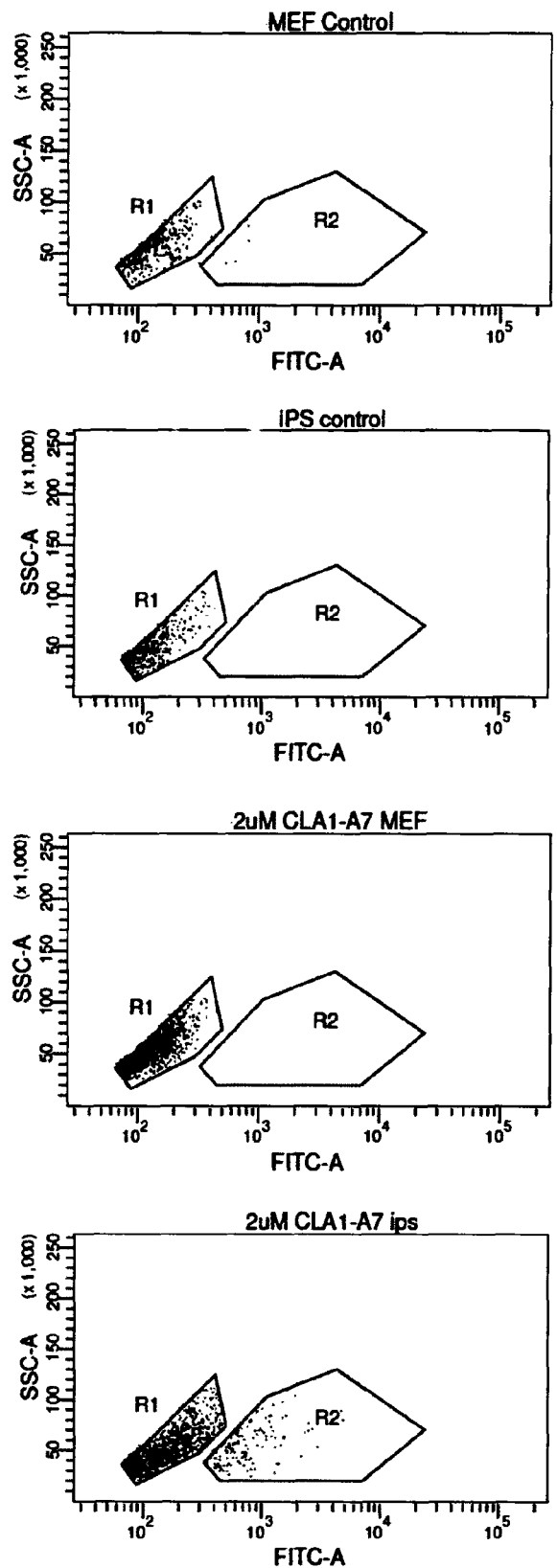
FIG. 2 are plots demonstrating the selective staining of 4 dpi (day of post induction) iPS by CDg4 using FACS. The iPS cells were maintained in mESC culture medium which was changed every day until designated time point. 4 dpi iPS was incubated with 2 μM of CDg4 for 1 hr at 37° C. The cells were harvested by trypsin treatment, washed with PBS and resuspended in PBS. The cells gated into SSClow CDg4 bright (R2) and SSChigh CDg4 dim (R1) regions were collected using a FACS machine (BD FACSAria™).

A description of example embodiments of the invention follows. The teachings of all patents, published applications and references cited herein are incorporated by reference in their entirety.

Chalcones are 1,3-diphenyl-2-propene-1-one compounds, in which two aromatic rings are linked by a three carbon α,β-unsaturated carbonyl system. Chalcones are abundant in edible plants and are considered to be precursors of flavonoids and isoflavonoids. Compounds incorporating the chalcone backbone have been reported to possess various biological activities, such as antimicrobial, anti-inflammatory, analgesic, antiplatelet, antiulcerative, antimalarial, anticancer, antiviral, antileishmanial, antioxidant, antitubercular, antihyperglycemic, immunomodulatory activities. (See (a) Mokle S S, et al., *Int. J. Chem. Sci.* 2004, 2(1), 96. (b). Hsieh H K, et al., *J. Pharm. Pharmacol.*, 2000, 52, 163. (c) Viana G S, et al., *J. Phytomedicine*, 2003, 10, 189. (d) Zhao L M, et al., *Bioorg. Med. Chem. Lett*, 2005, 15, 5027. (e) Mukarami S, et al., *Biochem. Pharmacol*, 1991, 42, 1447. (f) Liu M, et al., *J. Med. Chem.*, 2001, 44, 4443. (g) Francesco E, et al., *Phytochem*, 2007, 68, 939. (h) Onyilagna J C, et al., *Can. J. Plant Pathol*, 1997, 19, 133. (i) Nielsen S F, et al., *Bioorg. Med. Chem. Lett*, 1995, 5, 449. (j) Miranda C L, et al., *J. Agric. Food Chem*, 2000, 48, 3876. (k) Siva Kumar P M, et al., *Chem. Pharm. Bull.*, 2007, 55(1), 44. (l) Satyanarayana M, et al., *Bioorg. Med. Chem.*, 2004, 12, 883. (m) Barford L, et al., *Int. Immunopharmacol*, 2002, 2, 545, the entire teaching of are incorporated herein by reference.)

The photophysical and photochemical properties of chalcones derivatives have been of considerable interest for a long time because of their donor-acceptor ability and because they are readily functionalized, but not many cases of their use as a fluorescence dye have been reported. (See (a) P. F. Wang, S. K. Wu, *J. Photochem. Photobiol. A* 86 (1995) 109. (b) C-G Niu, et al., *Analytica Chimica Acta* 577 (2006) 264-270, the entire teachings of each are incorporated herein by reference.) We report herein novel fluorescent chalcone compounds synthesized via solid phase support synthetic method. One embodiment of the invention is a compound represented by the following chemical formula, designated CDgreen4 (or CDg4), λex/λem=430/560 nm):

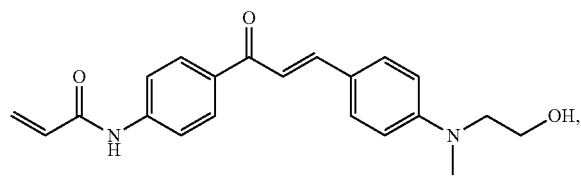 [SMILES: C=CC(=O)Nc1ccc(C(=O)/C=C/c2ccc(N(C)CCO)cc2)cc1]

or a salt thereof.

CDgreen4 selectively stains embryonic stem cells (ESC) and iPSC in a feeder cell-based culture system.

One embodiment of this invention is a method of isolating embryonic stem cells comprising the step of staining the cells with a chalcone derivative, or salt thereof, of the invention. In a particular embodiment, the chalcone derivative is CDg4 or a salt thereof.

Each stage of embryonic stem cell (ESC) can be monitored by immunocytochemistry methods. ESC can be characterized by high level expression of Oct-3/4 (also termed Oct-3 or Oct-4), a member of the POU transcription factors, and Nanog. A critical amount of Oct-3/4 and Nanog expression is required to sustain stem-cell pluripotency. When ESC are induced to differentiate, Oct-3/4 and Nanog are down-regulated, which has been proven to be essential for a proper and divergent developmental program.

After the ESCs have been stained with the chalcone compounds of the invention, the cells can be sorted. Cell surface antigens and alkaline phosphatase are biomarkers and may be used for stem cell confirmation. We have done for this confirmation experiment after sorting out by CDg4 with the biomarkers described in the following paragraphs.

The undifferentiated state of ES cells is often characterized by the expression of the cell surface antigens, SSEA-1, SSEA-3 and SSEA-4. SSEA-1 is expressed on the surface of preimplantation-stage murine embryos at the eight-cell stage and has been found on the surface of teratocarcinoma stem cells but not on their differentiated derivatives. SSEA-3 and SSEA-4 are synthesized during oogenesis and are present in the membranes of oocytes, zygotes and early cleavage-stage embryos. It has been suggested that the biological role of these carbohydrate-associated molecules is to control cell surface interactions during development. Undifferentiated primate ES cells, human ES cells and human embryonic carcinoma (EC) cells express SSEA-3 and SSEA-4, but not SSEA-1. Undifferentiated mouse ES cells, however, do express SSEA-1, but do not express SSEA-3 or SSEA-4.

Alkaline phosphatase is an enzyme in the blood, intestines, liver, and bone cells and exists as membrane-bound isoforms of glycoproteins sharing a common protein structure but differing in carbohydrate content. These enzymes are most active at alkaline pH—hence the name. Undifferentiated human EC, ES and embryonic germ (EG) cells have been shown to express a very high level of the liver/bone/kidney isozyme of alkaline phosphatase. Expression levels of alkaline phosphatase decrease following stem cell differentiation.

"Alkyl" means an optionally substituted saturated aliphatic branched or straight-chain monovalent hydrocarbon radical having from 1 to 16 carbon atoms. Alternatively, an alkyl group may have from 1 to 11 carbon atoms, 1 to 6 carbon atoms, 1 to 4 carbon atoms, 4 to 16 carbon atoms, 6 to 12 carbon atoms, 6 to 10 carbon atoms, or 10 to 16 carbon atoms. For example, "(C1-C6) alkyl" means a radical having from 1-6 carbon atoms in a linear or branched arrangement. "(C1-C6)alkyl" includes methyl, ethyl, propyl, butyl, pentyl and hexyl.

As used herein, the term "alkenyl" means a straight chain or branched non-cyclic hydrocarbon having from 2 to 16 carbon atoms and having at least one carbon-carbon double bond. Alternatively, an alkenyl group may have from 2 to 12 carbon atoms, 2 to 6 carbon atoms, 2 to 4 carbon atoms, 4 to 16 carbon atoms, 6 to 12 carbon atoms, 6 to 10 carbon atoms, or 10 to 16 carbon atoms. Alkenyl groups may be optionally substituted with one or more substituents at any substitutable hydrogen atom. For example, —CH=CH$_2$ may be substituted at a hydrogen atom with fluorine to yield —CF=CH$_2$, —CH=CFH, —CH=CF$_2$, —CF=CFH, —CH=CF$_2$, or —CF=CF$_2$.

As used herein, the term "alkynyl" means a straight chain or branched non-cyclic hydrocarbon having from 2 to 16 carbon atoms and having at least one carbon-carbon triple bond. Alternatively, an alkynyl group may have from 2 to 12 carbon atoms, 2 to 6 carbon atoms, 2 to 4 carbon atoms, 4 to 16 carbon atoms, 6 to 12 carbon atoms, 6 to 10 carbon atoms, or 10 to 16 carbon atoms. Alkynyl groups may be optionally substituted with one or more substituents at any substitutable hydrogen atom.

"Halogen" and "halo" are interchangeably used herein and each refers to fluorine, chlorine, bromine, or iodine. As used herein, halo-substituted-($C_1$-$C_{16}$)alkyl means a ($C_1$-$C_{16}$) alkyl substituted with one or more halogen groups. Examples of halo-substituted-($C_1$-$C_4$)alkyl include, but are not limited to —CF$_3$, —CH$_2$CF$_3$, —CH$_2$CF$_2$H, —CH$_2$CH$_2$F, —CH$_2$CH$_2$CF$_3$, —CCl$_3$, —CH$_2$CCl$_3$, —CH$_2$CCl$_2$H, —CH$_2$CH$_2$Cl and —CH$_2$CH$_2$CCl$_3$.

"Alkoxy" means an alkyl radical attached through an oxygen linking atom. "(C1-C6)-alkoxy" includes methoxy, ethoxy, propoxy, butoxy, pentoxy and hexoxy.

"Haloalkyl" and "halocycloalkyl" include mono, poly, and perhaloalkyl groups where each halogen is independently selected from fluorine, chlorine, and bromine.

"Carbocyclyl" means a cyclic group with only ring carbon atoms. "Carbocyclyl" includes 3-12-membered saturated or unsaturated aliphatic cyclic hydrocarbon rings or 6-12-membered aryl rings. Carbocyclyls are saturated or unsaturated aliphatic cyclic hydrocarbon rings or aromatic hydrocarbon rings having the specified number of carbon atoms. Carbocyclyls include cycloalkyl, cycloalkenyl, cycloalkynyl and aryl.

"Cycloalkyl" means a saturated aliphatic cyclic hydrocarbon ring. Thus, "$C_3$-$C_9$ cycloalkyl" means a hydrocarbon radical of a (3-9-membered) saturated aliphatic cyclic hydrocarbon ring. A $C_3$-$C_9$ cycloalkyl includes, but is not limited to cyclopropyl, cyclobutyl, cyclopentyl, cyclohexyl, cycloheptyl, cyclooctyl, and cyclononyl.

"Cycloalkene" means an aliphatic cyclic hydrocarbon ring having one or more double bonds in the ring. For example, cyclohexene is a cycloalkene.

"Cycloalkyne" means an aliphatic cyclic hydrocarbon ring having one or more triple bonds in the ring.

"Aryl" or "aromatic" means an aromatic monocyclic or polycyclic (e.g., bicyclic or tricyclic) carbocyclic ring system. In one embodiment, "aryl" is a 6-12-membered monocylic or bicyclic system. Aryl systems include, but are not limited to, phenyl, naphthalenyl, fluorenyl, indenyl, azulenyl, and anthracenyl. Aryl rings are optionally substituted with one or more groups independently selected from the following: halo, $NO_2$, —NHCO($C_1$-$C_6$)alkyl, —OCO($C_1$-$C_6$)alkyl, —COO($C_1$-$C_6$)alkyl, ($C_1$-$C_{10}$)alkyl, halo($C_1$-$C_{10}$)alkyl, ($C_1$-$C_{10}$)alkoxy, —S($C_1$-$C_6$)alkyl, ($C_3$-$C_9$)cycloalkyl, aryl, and phenoxy. More specifically, the aryl ring is phenyl and is optionally substituted with one, two, three, four or five groups independently selected from halo, $NO_2$, —NHCO($C_1$-$C_6$)alkyl, —OCO($C_1$-$C_6$)alkyl, ($C_1$-$C_{10}$)alkyl, halo($C_1$-$C_4$)alkyl, ($C_1$-$C_{10}$)alkoxy, and phenyl. Substituted phenyl rings may be mono substituted, and include, for example, the following structures:

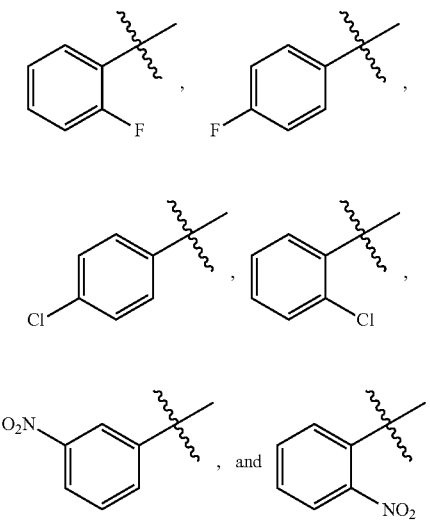

Substituted phenyl rings may be di-substituted, and include, for example, the following structures:

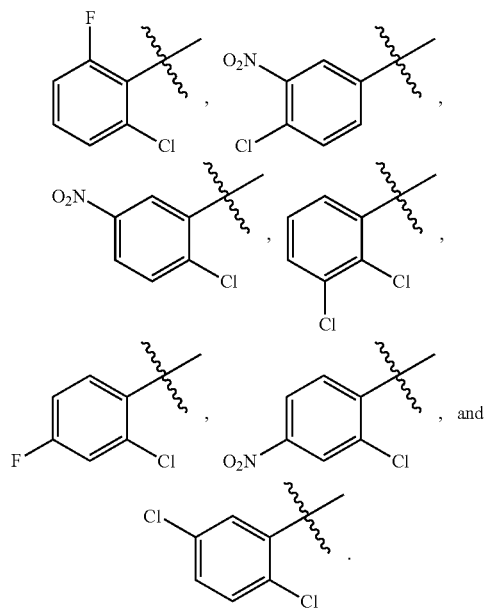

Similarly, the phenyl ring may optionally include three, four or five substituents that are the same or different.

The term "aryloxy," as used herein, means an "aryl-O—" group, wherein aryl is defined above. Examples of an aryloxy group include phenoxy or naphthoxy groups.

"Phenoxy" means a phenyl ring connected through an oxygen atom and is represented by the following structural formula:

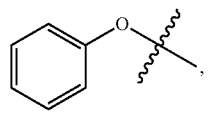 [SMILES: *Oc1ccccc1]

wherein ⸹ indicates connectivity to the remainder of the molecule. Phenoxy moieties may be optionally substituted with one, two, three, four or five groups independently selected from halo, $NO_2$, —NHCO($C_1$-$C_6$)alkyl, —OCO($C_1$-$C_6$)alkyl, halo($C_1$-$C_4$)alkyl, ($C_1$-$C_{10}$)alkoxy, and phenyl. Examples of substituted phenoxy include, for example the following representative chemical structures:

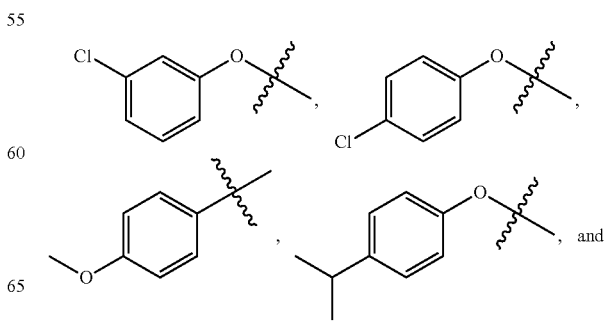

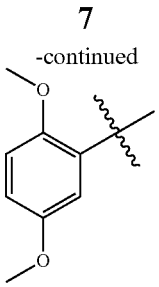

"Hetero" refers to the replacement of at least one carbon atom member in a ring system with at least one heteroatom selected from N, S, and O. "Hetero" also refers to the replacement of at least one carbon atom member in an acyclic system. A hetero ring system or a hetero acyclic system may have 1, 2, 3 or 4 carbon atom members replaced by a heteroatom.

"Heterocyclyl" means a cyclic 4-12-membered saturated or unsaturated aliphatic or aromatic ring containing 1, 2, 3, 4 or 5 heteroatoms independently selected from N, O or S. When one heteroatom is S, it can be optionally mono- or di-oxygenated (i.e., —S(O)— or —S(O)$_2$—). The heterocyclyl can be monocyclic, bicyclic, or polycyclic.

"Saturated heterocyclyl" means an aliphatic heterocyclyl group without any degree of unsaturation (i.e., no double bond or triple bond).

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

Polycyclic heterocyclyls have more than two rings, one of which is a heterocyclyl (e.g., three rings resulting in a tricyclic ring system) and adjacent rings having at least one ring atom in common.

"Heteroaryl" or "heteroaromatic ring" means a 5-12-membered monovalent heteroaromatic monocyclic or bicylic ring radical. A heteroaryl contains 1, 2, 3 or 4 heteroatoms independently selected from N, O, and S. Heteroaryls include, but are not limited to, furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to indolizine, indole, isoindole, indazole, benzimidazole, benzthiazole, benzothiophene, purine, quinoline, isoquinoline, cinnoline, phthalazine, quinazoline, quinoxaline, 1,8-naphthyridine, and pteridine.

EXEMPLIFICATION

Design of Chalcone Derivatives

Most fluorescent chemosensors employ an increase or decrease in their emission intensity as a sensing signal in response to the surrounding medium or through specific molecular recognition events. Due to their simplicity and high sensitivity, fluorescent sensors have been widely utilized as tools for chemical, biological, and medical applications. Sensors are prepared via two different strategies. For "Analyte Directed Sensors," the fluorescence dye molecules are combined with designed receptors for a specific analyte. Alternatively, "Diversity Directed Sensors" are generated via a combinatorial dye library and can be developed for a diverse set of dyes.

The invention is based on the synthesis of a new fluorescence dye of chalcone structure:

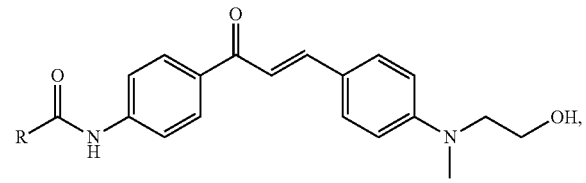

or a salt thereof, where R is as defined above, which shows fluorescence emission sensitivity depending upon the polarity of solvent and pH. The central ketone group has electron accepting properties which can make it suitable for use as a fluorescence emission dye.

General Methods.

All reactions were performed in oven-dried glassware under a positive pressure of nitrogen. Unless otherwise noted, starting materials and solvents were purchased from Aldrich and Acros Organics and used without further purification. Analytical TLC was carried out on Merck 60 F254 silica gel plate (0.25 mm layer thickness) and visualization was done with UV light. Column chromatography was performed on Merck 60 silica gel (230-400 mesh). NMR spectra were recorded on a Bruker Avance 300 NMR spectrometer. Chemical shifts are reported as δ in units of parts per million (ppm) and coupling constants are reported as a J value in Hertz (Hz). Mass of all the compounds was determined by LC-MS of Agilent Technologies with an electrospray ionization source. All fluorescence assays were performed with a Gemini XS fluorescence plate reader.

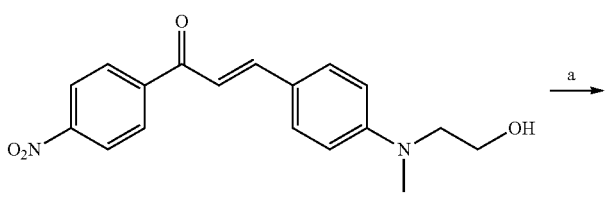 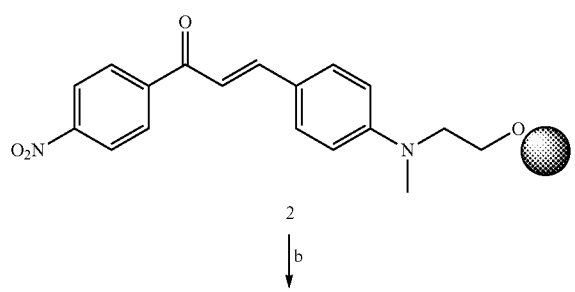

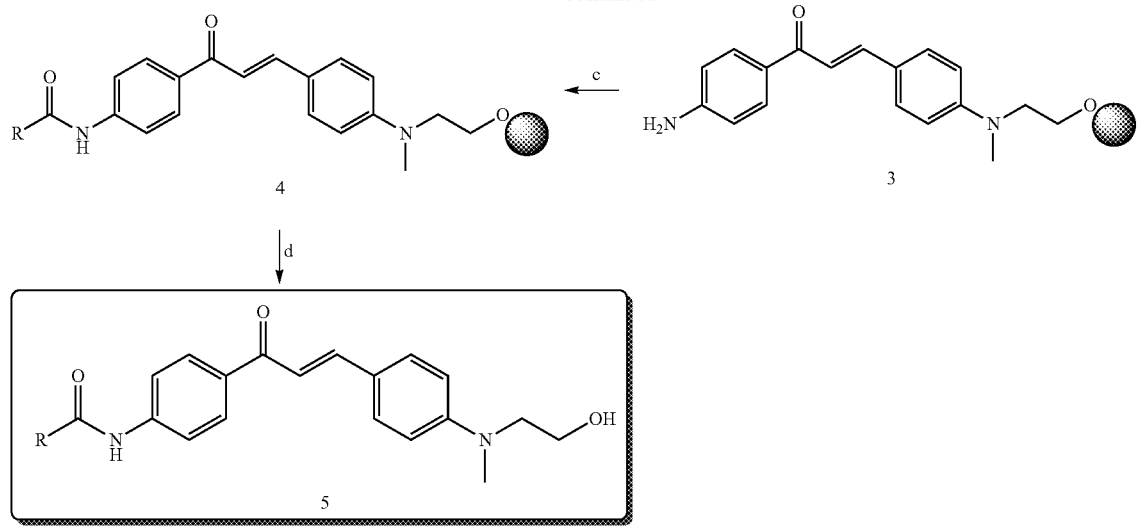

(a) ClTr-Cl resin, Py, DCM, 5 hrs. RT, (b) 2M SnCl$_2$, 2H$_2$O in DMF, RT, 16 hrs, (c) RCOCl, Py, DCM, 30 min, (d) 2% TFA in DCM

Chemical Synthesis

Synthesis of Compound 1:

To the solution of 4'-nitroacetophenone (100 mg, 0.6 mmol) and N,N'-2-hydroxyethyl, methyl nitrobenzaldehyde (100 mg, 0.55 mmol) in ethanol (EtOH), pyrrolidine (0.1 mL) was added and heated with commercial Microwave Reactor (150 MW) for 3 minutes. The resultant solution was cooled and kept at the room temperature for 2 hours, after which a dark red solid precipitated. The solid was filtered and washed with ethyl acetate and hexanes (1:1) solution and dried as a dark red solid (100 mg, 60%). Obtained solid was used for subsequent reaction without any purification.

Synthesis of Compound 2:

2-Chlorotrityl resin (200 mg, 1 mmol/g) was pre-swelled in DCM. To the resin solution, compound 1 (100 mg) and 3 equivalents of pyridine were added and the reaction mixture was stirred overnight. The reaction mixture was filtered and washed with DMF, MeOH, DCM after 1 hour MeOH capping procedure for extra resin chloride deactivation. Washed resin was dried with high vacuum dessicator and used without further purification.

Synthesis of Compound 5:

Resin loaded with compound 2 was treated with SnCl$_2$ hydrate (20 equivalents) in DMF solution. The reaction mixture was shaken overnight and washed with DMF, MeOH, DCM. After high vacuum drying, the resin (60 mg) was aliquoted into each 5 mL syringe. The reaction syringes were washed with DCM and pyridine (3 equivalents) in DCM (1 mL) was loaded in syringe and acid chlorides (RCOCl) in 2 mL loading was followed to yield compound 3, which was used without further purification. The reaction syringes were shaken for 30 minutes, and then were washed out with DCM, MeOH, DCM.

Cleavage Protocol:

1% TFA in DCM solution was loaded for cleavage. For 30 minutes, incubated with cleavage solution, aliquot was squeezed out and collected in 20 mL vial. 2.5% ammonia water in ACN was added for TFA neutralization and then filtered through a silica end-filled tip. Dark brown solid was obtained after removing solvent and purity was analyzed by LC/MS.

Characteristics of Representative Compounds

CDg4 was synthesized according to the general synthetic procedure. 1H-NMR (CDCl$_3$) δ 10.61 (s, 1H, NH), 8.11 (d, J=8.1, 2H), 7.85 (d, J=8.1, 2H), 7.66 (d, J=8.7, 2H), 7.63 (bs, 2H), 6.74 (d, J=8.4, 2H), 6.52 (m, 1H), 6.30 (d, J=16.5, 1H), 5.80 (d, J=9.9, 1H), 5.74 (s, 1H), 4.76 (bs, 1H), 3.58 (bs, 2H), 3.48 (bd, 2H), 3.01 (s, 3H); $^{13}$C-NMR (CDCl$_3$) δ 187.50, 163.94, 151.45, 144.95, 143.28, 133.70, 131.11, 129.80, 127.97, 122.10, 119.09, 116.17, 111.85, 104.90, 58.51, 54.27, 48.97. ESI-MS m/z (M+H) calc'd: 351.1. found 351.1, FAB-MS MS m/z (M+H) calc'd: 351.1. found 351.1.

Fluorescence Property Measurement

Figure 3:
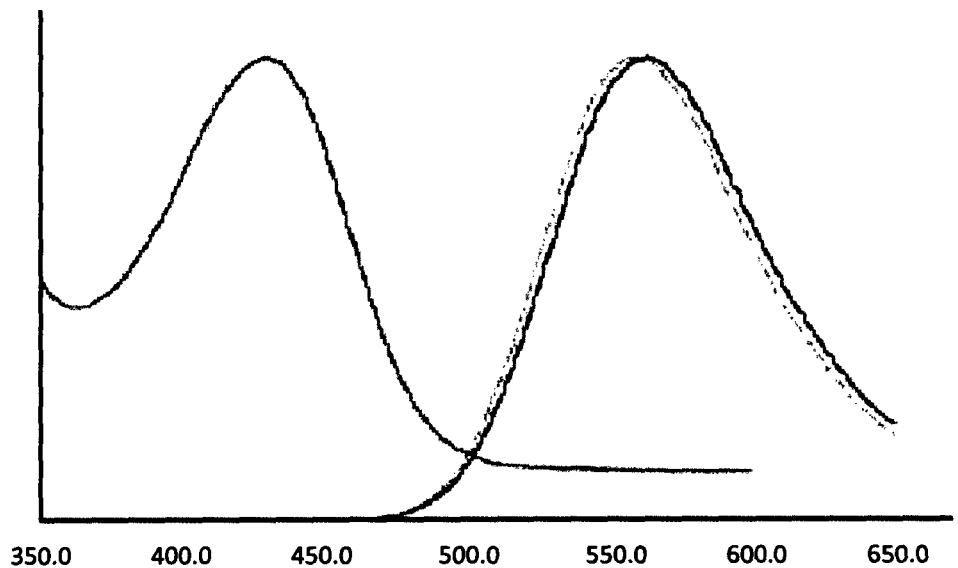
FIG. 3 is a representative graph depicting the fluorescence measurement of the chalcone derivatives of this invention.

10 μM solutions in DMSO were prepared and the absorption and emission of library compounds was measured. FIG. 3 is a representative absorbance and fluorescence spectrum. The spectral information is as follows:

| Spectral Information | |
| --- | --- |
| ABS (nm) | 429 |
| Excitation (nm) | 430 nm |
| C (abs) | 50 μm |
| Em (nm) | 563 |
| Max RFU | 25709 |
| C (em) | 10 μm |
| Quantum Yield | 0.202 |

Measurements for the other chalcone compounds are presented in FIG. 1.

Identification of Chalcone Derivatives

To evaluate the application of chalcone derivatives as ESC-selective probes, 320 chalcone compounds were screened in mouse ESC (mESC) and mouse embryonic fibroblast (MEF) feeder cells prepared on 384-well cell culture microplates. From the image-based primary screening, 8 compounds that stained mESC consistently with stronger intensity than MEF were selected. For the secondary screening, mESC and MEF were incubated separately with each of the hit compounds and subsequently analyzed using flow cytometry. The flow cytometry data of side scatter (SSC) and fluorescence intensity in dot plot overlay of mESC and MEF indicated CDg4 as the most selective for mESCs among the 8 hit compounds.

Enrichment of mESC Using FACS

Figure 4:
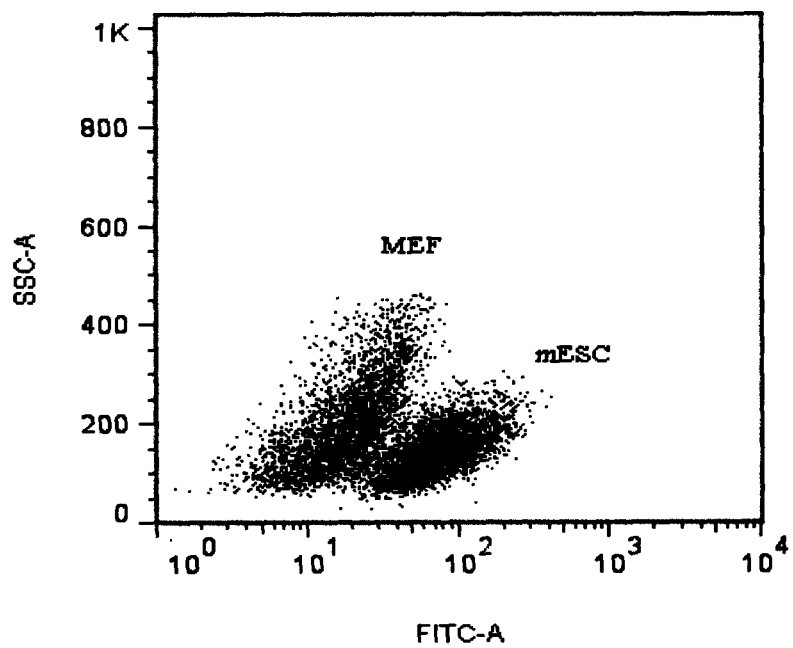
FIG. 4 shows a flow cytometry dot plot image of CDg4 stained mESC and MEF.

To confirm the secondary screening data, a mixture of mESC and MEF was incubated with CD4. The cell mixture was sorted using Fluorescence-Activated Cell Sorting (FACS). Fluorescence microscopy demonstrated that live mESC cultured on MEF feeder are much more brightly stained by CDg4 than MEF. The data demonstrated that CD4 can be used for mESC enrichment from a mixed-cell population. FIG. 4 shows a flow cytometry dot plot image of CDg4 stained mESC and MEF.

Co-Localization of CDg4 and CellMask-Plasma Membrane.

mESC were incubated with 2 µM CDg4, 5 ug/mL CELL-MASK® Deep Red Plasma membrane stain and 4 µg/ml Hoechst for 30 minutes at 37° C. and washed with PBS two times. The images were taken using a Nikon ECLIPSE Ti fluorescence microscope equipped with a 60× objective lens.

Use of CDg4 to Isolate Early iPS Cells to Study DNA Profile with DNA Microarray.

CDg4 was applied to induced pluripotent stem cell (iPSC) which was generated from MEF of transgenic mice that express GFP under the control of Oct4 (also known as Pou5f1) promoter. CDg4 selectively stained the iPSC colony. FACS was used to isolate early iPS cell population stained by CDg4. (FIG. 2). Isolation of the early iPS cell population will facilitate gene profiling using DNA microarray of this cell population. While gene expression profiling for mixture populations or using cell lines are reported, with lack of direct marker or probes for early iPS, it was not possible to study with purified early iPS.

DNA microarray analysis for their gene expression pattern will be performed to understand the mechanism and events for the difference of early and late stage of cell reprogramming. CDg4-stained cells will be sorted out using FACS and their RNA will be isolated. Biotinylated cRNA using Illumina RNA Amplification Kit (Ambion Inc.) will be synthesized and hybridized to BeadChips. Arrays will be scanned and analyzed using iScan Scanner System and GenePlex software. Our CDg4 will provide a unique chance to isolate and enrich the specific populations.

General Experimental Methods:

Cell Culture.

mESC was cultured in a culture dish coated with 0.1% gelatin using a high-glucose Dulbecco's Modified Eagle's medium (DMEM) supplemented with 10% fetal calf serum, 2 mM L-glutamine, 100 U/ml penicillin, 100 µg/ml streptomycin, 0.1 mM non-essential amino acids, 0.1% β-mercaptoethanol and 100 U/ml leukemia inhibitory factor (LIF, Chemicon). MEF was maintained in the same media as used for mESC without LIF and treated with mitomycin C (10 µg/ml) before used as feeder cell.

Image-Based Cell Screening.

MEFs were plated on 0.1% gelatin-coated 384-well cell culture microplates (Greiner bio-one, Germany). On the next day, mESCs were plated both on MEF feeder and feeder-free wells for overnight culture and then incubated with 1 uM of chalcone fluorescent compounds. After 0.5 hours, 24 hours and 48 hours, FITC fluorescence and bright field images were taken using ImageXpressMICRO imaging system (Molecular Devices).

Flow Cytometry and FACS.

MEFs and mESCs were cultured in 60 mm culture dish for 1 hour in the presence of 2 µM of hit compounds, including CDg4. The cells were harvested by trypsin treatment, washed with PBS and resuspended in PBS. The fluorescence intensity of the cells was measured on Flow Cytometry (BD™ LSR II) with FITC (excitation at 530 nm, emission at 560 nm). The dot plot images for each cell type were overlaid using FlowJo7 (Three Star Inc.) For FACS MEF and mESC were cultured in a same dish and the sample was prepared as described above for flow cytometry. The cells gated into SSClow CDgreen4 bright and SSChigh CDgreen4 dim regions were collected using a FACS machine (BD FACSAria™).

iPSC Generation.

The retroviral packaging cell, PlatE cell, was maintained in DMEM containing 10% FBS, 100 U/ml penicillin, 100 µg/ml streptomycin, 10 µg/ml blasticidin 5 and 1 µg/ml puromycin. For the generation of retroviruses, 40 µg of each retroviral vectors expressing each mouse Oct4, Sox2, Klf4, and c-Myc was transfected together using Lipofectamine 2000™ (Invitrogen) into PlatE cells plated at a density of $8 \times 10^6$ cells/10 cm cell culture dish and cultured overnight in DMEM containing only 10% FBS. Medium was changed 5 hours after transfection to normal maintenance medium and incubated further in a humidified atmosphere of 5% $CO_2$ and 95% air at 37° C. Culture supernatant was harvested 48 hours after transfection, filtered through a 0.45-µm syringe filter, concentrated by using Amicon Ultra-15 Centrifugal filter units (Millipore) and stored at −80° C. until use. For reprogramming, MEFs prepared from E13.5 B6; CBA-Tg(Pou5f1-EGFP)2Mnn/J mouse (Jackson Laboratory) embryo were plated at a density of $3 \times 10^4$ cells/well in a 24-well plate and infected with retroviruses mixture 8 hours later. Polybrene (Sigma) was added at a concentration of 10 µg/ml to increase virus adsorption. Infected MEFs were harvested 48 hours later by trypsinization and plated onto mytomycin C treated MEF feeder cells. The cells were maintained in mESC culture medium which was changed every day until designated time points.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula:

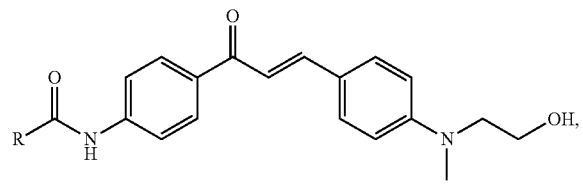

or a salt thereof, wherein:

R is $(C_1-C_{16})$alkyl, $(C_2-C_{16})$alkenyl, $(C_2-C_{16})$alkynyl, carbocyclyl or heterocyclyl, each of which is optionally substituted with one or more groups independently selected from the following: halo, $NO_2$, —NHCO($C_1$-$C_6$)alkyl, —OCO($C_1$-$C_6$)alkyl, —COO($C_1$-$C_6$)alkyl, $(C_1$-$C_{10})$alkyl, halo($C_1$-$C_{10}$)alkyl, $(C_1$-$C_{10})$alkoxy, —S($C_1$-$C_6$)alkyl, $(C_3$-$C_9$)cycloalkyl, aryl, and phenoxy, wherein each phenoxy or aryl are further optionally substituted with one or more groups selected from halo, $NO_2$, $(C_1$-$C_{10})$alkyl, halo($C_1$-$C_{10}$)alkyl, and $(C_1$-$C_{10})$alkoxy.

2. The compound of claim 1, or a salt thereof, wherein R is $(C_1$-$C_{16})$alkyl.

3. The compound of claim 2, or a salt thereof, wherein R is $(C_1$-$C_{11})$alkyl, optionally substituted with one, two or three groups independently selected from chloro, bromo, methyl, ethyl, methoxy, —COOCH₃, —OCOCH₃, cyclopentyl, phenyl, and phenoxy, wherein the phenyl or phenoxy is optionally and independently substituted with one, two, three, four, or five groups independently selected from fluoro, chloro, and methoxy.

4. The compound of claim 1, or a salt thereof, where the compound is represented by the following structural formulas:

[structural formulas]

or a salt thereof.

5. The compound of claim 1, or a salt thereof, wherein R is C₂-C₁₆)alkenyl.

6. The compound of claim 5, or a salt thereof, wherein R is —CH═CH₂, —CH₂CH₂C═CH₂, (CH₂)₈C═CH₂, optionally substituted with one or more substituents selected from methyl and phenyl, wherein the phenyl is optionally substituted with chloro.

7. The compound of claim 6, or a salt thereof, wherein the compound is represented by the following structural formula:

[structural formula]

or a salt thereof.

8. The compound of claim 1, or a salt thereof, wherein R is carbocyclyl.

9. The compound of claim 8, or a salt thereof, wherein R is an optionally substituted aryl.

10. The compound of claim 9, or a salt thereof, wherein R is an optionally substituted phenyl.

11. The compound of claim 10, or a salt thereof, wherein R is phenyl, optionally substituted with one, two, three, four or five groups independently selected from halo, NO₂, —NHCO(C₁-C₆)alkyl, —OCO(C₁-C₆)alkyl, (C₁-C₁₀)alkyl, halo(C₁-C₄)alkyl, (C₁-C₁₀)alkoxy, and phenyl.

12. The compound of claim 11, or a salt thereof, wherein R is phenyl, optionally substituted with one, two, three, four or five groups independently selected from fluoro, chloro, bromo, iodo, —NO₂, —NHCOCH₃, —OCOCH₃, methyl, ethyl, propyl, isopropyl, butyl, pentyl, hexyl, heptyl, nonyl, decyl, —CF₃, —CH₂Cl, methoxy, ethoxy, butoxy, hexoxy, heptoxy, and phenyl.

13. The compound of claim 9, or a salt thereof, wherein R is naphthyl, optionally substituted with one, two, three, four or five groups independently selected from halo, NO₂, —NHCO(C₁-C₆)alkyl, —OCO(C₁-C₆)alkyl, (C₁-C₁₀)alkyl, halo(C₁-C₄)alkyl, (C₁-C₁₀)alkoxy, and phenyl.

14. The compound of claim 13, or a salt thereof, wherein R is naphthyl, optionally substituted with ethoxy.

15. The compound of claim 8, or a salt thereof, wherein R is (C₃-C₉)cycloalkyl, optionally substituted with one or two groups independently selected from halo, NO₂, —NHCO(C₁-C₆)alkyl, —OCO(C₁-C₆)alkyl, (C₁-C₁₀)alkyl, halo(C₁-C₄)alkyl, (C₁-C₁₀)alkoxy, and phenyl.

16. The compound of claim 15, or a salt thereof, wherein R is cyclohexyl, cyclopentyl, cyclobutyl, or cyclopropyl.

17. The compound of claim 8, or a salt thereof, wherein R is (C₃-C₉)cycloalkenyl, optionally substituted with one or two groups independently selected from halo, NO₂, —NHCO(C₁-C₆)alkyl, —OCO(C₁-C₆)alkyl, (C₁-C₁₀)alkyl, halo(C₁-C₄)alkyl, (C₁-C₁₀)alkoxy, and phenyl.

18. The compound of claim 17, or a salt thereof, wherein R is cyclohexenyl.

19. The compound of claim 1, or a salt thereof, wherein R is heterocyclyl.

20. The compound of claim 19, or a salt thereof, wherein R is

[structural formula: morpholine]

21. The compound of claim 19, or a salt thereof, wherein R is optionally substituted heteroaryl.

22. The compound of claim 21, or a salt thereof, wherein R is optionally substituted heteroaryl selected from benzo[b]thiophene, furanyl, pyrrole, isoxazole, thiophene, pyridine, and pyrimidine.

23. The compound of claim 22, or a salt thereof, wherein R is selected from

[structural formulas of heteroaryl groups]

or

[structural formula]

wherein each R is optionally substituted with one, two, or three groups independently selected from fluoro, chloro, bromo, —NO₂, methyl, methoxy, —SCH₃, and phenyl, wherein the phenyl is optionally substituted with one, two or three groups independently selected from fluoro, chloro, and NO₂.

24. A method for the preferential staining of stem cells, comprising incubating a cell population comprising stem cells with a compound of Formula (I) or a salt thereof:

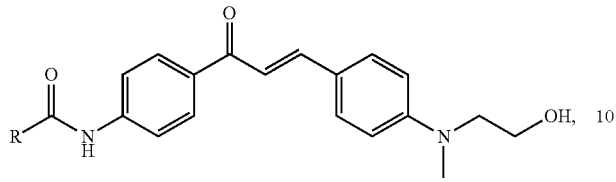

(I)

wherein:
R is $(C_1-C_{16})$alkyl, $(C_2-C_{16})$alkenyl, $(C_2-C_{16})$alkynyl, carbocyclyl or heterocyclyl, each of which is optionally substituted with one or more groups independently selected from the following: halo, $NO_2$, —NHCO$(C_1-C_6)$alkyl, —OCO$(C_1-C_6)$alkyl, —COO$(C_1-C_6)$alkyl, $(C_1-C_{10})$alkyl, halo$(C_1-C_{10})$alkyl, $(C_1-C_{10})$alkoxy, —S$(C_1-C_6)$alkyl, $(C_3-C_9)$cycloalkyl, aryl, and phenoxy, wherein each phenoxy or aryl are further optionally substituted with one or more groups selected from halo, $NO_2$, $(C_1-C_{10})$alkyl, halo$(C_1-C_{10})$alkyl, and $(C_1-C_{10})$alkoxy;

for a period of time sufficient to stain stem cells, wherein stem cells are stained with greater intensity by fluorescence than any other cell types.

25. The method of claim 24, further comprising sorting the stained stem cells from the remaining cell population.

26. The method of claim 25, wherein the sorting is Fluorescence Activated Cell Sorting (FACS).

27. The method of claim 24, wherein the compound of Formula (I) is:

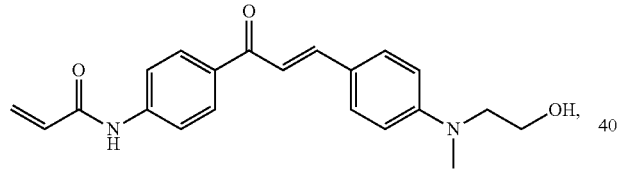

or a salt thereof.

28. The method of claim 24, wherein the stem cells are embryonic stem cells.

29. The method of claim 24, wherein the stem cells are induced pluripotent stem cells.

30. A method of visualizing a stem cell, comprising:

a) contacting a cell population with a compound of formula (I) or a salt thereof:

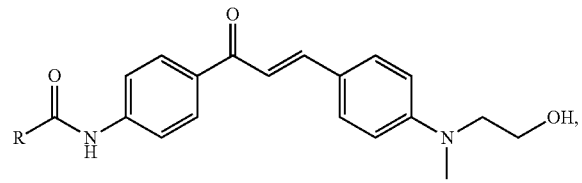

(I)

wherein:
R is $(C_1-C_{16})$alkyl, $(C_2-C_{16})$alkenyl, $(C_2-C_{16})$alkynyl, carbocyclyl or heterocyclyl, each of which is optionally substituted with one or more groups independently selected from the following: halo, $NO_2$, —NHCO$(C_1-C_6)$alkyl, —OCO$(C_1-C_6)$alkyl, —COO$(C_1-C_6)$alkyl, $(C_1-C_{10})$alkyl, halo$(C_1-C_{10})$alkyl, $(C_1-C_{10})$alkoxy, —S$(C_1-C_6)$alkyl, $(C_3-C_9)$cycloalkyl, aryl, and phenoxy, wherein each phenoxy or aryl are further optionally substituted with one or more groups selected from halo, $NO_2$, $(C_1-C_{10})$alkyl, halo$(C_1-C_{10})$alkyl, and $(C_1-C_{10})$alkoxy;

to form an incubation media;

b) incubating the incubation media of step (a) for a period of time sufficient to stain the stem cells; and c) visualizing the stained cells of step (b) with fluorescence microscopy to visualize a stem cell.

31. The method of claim 30, wherein the stem cell is an embryonic stem cell.

* * * * *

UNITED STATES PATENT AND TRADEMARK OFFICE
CERTIFICATE OF CORRECTION

| | |
|---|---|
| PATENT NO. | : 8,871,976 B2 |
| APPLICATION NO. | : 13/817898 |
| DATED | : October 28, 2014 |
| INVENTOR(S) | : Young-Tae Chang, Sung Chan Lee and Nam Young Kang |

Page 1 of 1

It is certified that error appears in the above-identified patent and that said Letters Patent is hereby corrected as shown below:

In the Claims

Column 13, Claim 5, line 29, please delete "$c_2$-$c_{16}$)" and insert -- ($c_2$-$c_{16}$) --.

Signed and Sealed this
Nineteenth Day of May, 2015

Michelle K. Lee
*Director of the United States Patent and Trademark Office*